(12) United States Patent
Manaresi et al.

(10) Patent No.: US 10,895,575 B2
(45) Date of Patent: *Jan. 19, 2021

(54) METHOD FOR IDENTIFICATION, SELECTION AND ANALYSIS OF TUMOUR CELLS

(71) Applicant: Menarini Silicon Biosystems S.p.A., Castel Maggiore (IT)

(72) Inventors: Nicolò Manaresi, Bologna (IT); Gianni Medoro, Casalecchio di Reno (IT); Giuseppe Giorgini, Padua (IT)

(73) Assignee: Menarini Silicon Biosystems S.p.A., Castel Maggiore (IT)

( * ) Notice: Subject to any disclaimer, the term of this patent is extended or adjusted under 35 U.S.C. 154(b) by 0 days.

This patent is subject to a terminal disclaimer.

(21) Appl. No.: 14/542,259

(22) Filed: Nov. 14, 2014

(65) Prior Publication Data

US 2015/0126396 A1 May 7, 2015

Related U.S. Application Data

(63) Continuation-in-part of application No. 13/127,640, filed as application No. PCT/IB2009/007316 on Nov. 4, 2009, now Pat. No. 10,234,447.

(30) Foreign Application Priority Data

Nov. 4, 2008 (IT) .............................. TO2008A0814

(51) Int. Cl.
*G01N 33/574* (2006.01)

(52) U.S. Cl.
CPC ..... *G01N 33/57423* (2013.01); *G01N 33/574* (2013.01)

(58) Field of Classification Search
None
See application file for complete search history.

(56) References Cited

U.S. PATENT DOCUMENTS

| | | |
|---|---|---|
| 4,682,007 A | 7/1987 | Hollander |
| 4,956,298 A | 9/1990 | Diekmann |
| 4,990,253 A | 2/1991 | Vcelka |
| 5,252,493 A | 10/1993 | Fujiwara et al. |
| 5,279,493 A | 1/1994 | Halder |
| 5,556,598 A | 9/1996 | Raybuck et al. |
| 5,833,860 A | 11/1998 | Kopaciewicz et al. |
| 5,888,370 A | 3/1999 | Becker et al. |
| 5,888,730 A | 3/1999 | Gray et al. |
| 5,942,443 A | 8/1999 | Parce et al. |
| 5,945,281 A | 8/1999 | Prabhu |
| 6,071,394 A * | 6/2000 | Cheng .............. B01D 57/02 204/547 |
| 6,149,489 A | 11/2000 | Johnson |
| 6,149,789 A | 11/2000 | Benecke et al. |
| 6,203,683 B1 | 3/2001 | Austin et al. |
| 6,264,815 B1 | 7/2001 | Pethig et al. |
| 6,294,063 B1 | 9/2001 | Becker et al. |
| 6,824,664 B1 | 11/2004 | Austin et al. |
| 6,830,729 B1 | 12/2004 | Holl et al. |
| 6,875,329 B2 | 4/2005 | Washizu et al. |
| 6,888,721 B1 | 5/2005 | Moghaddam et al. |
| 6,911,132 B2 | 6/2005 | Pamula et al. |
| 6,977,033 B2 | 12/2005 | Becker et al. |
| 7,147,763 B2 | 12/2006 | Elrod et al. |
| 7,250,933 B2 | 7/2007 | De Boer et al. |
| 7,307,328 B2 | 12/2007 | Meyer et al. |
| 7,488,406 B2 | 2/2009 | Hughes et al. |
| 7,641,779 B2 | 1/2010 | Becker et al. |
| 8,216,513 B2 | 7/2012 | Becker et al. |
| 8,349,160 B2 | 1/2013 | Medoro et al. |
| 8,388,823 B2 | 3/2013 | Manaresi et al. |
| 8,641,880 B2 | 2/2014 | Medoro et al. |
| 8,679,856 B2 | 3/2014 | Manaresi |
| 8,685,217 B2 | 4/2014 | Manaresi et al. |
| 9,310,287 B2 | 4/2016 | Medoro et al. |
| 9,581,528 B2 | 2/2017 | Manaresi |
| 9,719,960 B2 | 8/2017 | Medoro et al. |

(Continued)

FOREIGN PATENT DOCUMENTS

| | | |
|---|---|---|
| DE | 3931851 C2 | 4/1992 |
| DE | 10203636 B4 | 2/2004 |

(Continued)

OTHER PUBLICATIONS

Corver et al., High-Resolution Multiparameter DNA Flow Cytometry for the Detection and Sorting of Tumor and Stromal Subpopulations from Paraffin-Embedded Tissues; Current Protocols in Cytometry, 6.27.1-6.27.21, Oct. 2009.*
Altomare et al., Levitation and movement of human tumor cells using a printed circuit board device based on software-controlled dielectrophoresis, Biotechnol. Bioeng., 82(4):474-9 (2003).
Berthier et al., NSTI Nanotech 2005, vol. 1 (2005), www.nsti.org.
Bonci et al., The miR-15a-miR-16-1 cluster controls prostate cancer by targeting multiple oncogenic activities, Nat. Med., 14:1271-7 (2008).

(Continued)

*Primary Examiner* — Nancy J Leith
(74) *Attorney, Agent, or Firm* — Marshall, Gerstein & Borun LLP

(57) ABSTRACT

The present invention relates to a method for the diagnosis of tumoural conditions and/or of the corresponding state of advance, wherein a sample from a patient comprising at least one tumour cell is obtained. According to the invention, a purified specimen of the at least one tumour cell is obtained by individually selecting and isolating single cells in a microfluidic device the purified specimen having a purity of at least 90%. On the purified specimen thus obtained there is subsequently performed a molecular analysis such as to highlight a characteristic thereof suited to enabling diagnosis.

28 Claims, 21 Drawing Sheets
Specification includes a Sequence Listing.

(56) References Cited

U.S. PATENT DOCUMENTS

| | | |
|---|---|---|
| 2002/0031838 A1 | 3/2002 | Meinhart et al. |
| 2002/0036139 A1 | 3/2002 | Becker et al. |
| 2002/0070114 A1 | 6/2002 | Miles |
| 2002/0125138 A1 | 9/2002 | Medoro |
| 2002/0132316 A1 | 9/2002 | Wang et al. |
| 2002/0172987 A1 | 11/2002 | Terstappen et al. |
| 2002/0195342 A1 | 12/2002 | Lee et al. |
| 2003/0044832 A1 | 3/2003 | Blankenstein |
| 2003/0047456 A1 | 3/2003 | Medoro |
| 2003/0069413 A1 | 4/2003 | Pai et al. |
| 2003/0073110 A1 | 4/2003 | Aritomi et al. |
| 2003/0098271 A1 | 5/2003 | Somack et al. |
| 2004/0011652 A1 | 1/2004 | Bressler |
| 2004/0055891 A1 | 3/2004 | Pamula et al. |
| 2004/0058450 A1 | 3/2004 | Pamula et al. |
| 2004/0063196 A1 | 4/2004 | Muller et al. |
| 2004/0149546 A1 | 8/2004 | Henson et al. |
| 2004/0159546 A1 | 8/2004 | Zhang et al. |
| 2004/0191789 A1 | 9/2004 | Manaresi et al. |
| 2004/0209354 A1 | 10/2004 | Mathies et al. |
| 2004/0229210 A1 | 11/2004 | Sabry et al. |
| 2005/0009101 A1 | 1/2005 | Blackburn |
| 2005/0014146 A1 | 1/2005 | Manaresi et al. |
| 2005/0112541 A1 | 5/2005 | Durack et al. |
| 2005/0214736 A1 | 9/2005 | Childers et al. |
| 2006/0029923 A1 | 2/2006 | Togawa et al. |
| 2006/0037903 A1 | 2/2006 | Smith et al. |
| 2006/0051775 A1 | 3/2006 | Bianchi |
| 2006/0057738 A1 | 3/2006 | Hall |
| 2006/0072804 A1 | 4/2006 | Watson et al. |
| 2006/0086309 A1 | 4/2006 | Manger et al. |
| 2006/0139638 A1 | 6/2006 | Muller et al. |
| 2006/0171846 A1* | 8/2006 | Marr ............... G01N 15/1459 422/82.11 |
| 2006/0177815 A1 | 8/2006 | Soh et al. |
| 2006/0223178 A1 | 10/2006 | Barber et al. |
| 2006/0228749 A1 | 10/2006 | Wang et al. |
| 2006/0290745 A1 | 12/2006 | Feng et al. |
| 2007/0015289 A1 | 1/2007 | Kao et al. |
| 2007/0026413 A1 | 2/2007 | Toner et al. |
| 2007/0026415 A1 | 2/2007 | Fuchs et al. |
| 2007/0051412 A1 | 3/2007 | Heath et al. |
| 2007/0059683 A1 | 3/2007 | Barber et al. |
| 2007/0172903 A1 | 7/2007 | Toner et al. |
| 2007/0190522 A1 | 8/2007 | Somack et al. |
| 2007/0195324 A1 | 8/2007 | Adams et al. |
| 2007/0250301 A1 | 10/2007 | Vaisberg et al. |
| 2008/0057572 A1 | 3/2008 | Petersen et al. |
| 2008/0058991 A1 | 3/2008 | Lee et al. |
| 2008/0246489 A1 | 10/2008 | Coster et al. |
| 2008/0264068 A1 | 10/2008 | Nakasuka et al. |
| 2009/0008254 A1 | 1/2009 | Muller et al. |
| 2009/0047216 A1* | 2/2009 | Coukos ............... C12Q 1/6886 424/9.1 |
| 2009/0205963 A1 | 8/2009 | Medoro et al. |
| 2009/0218223 A1 | 9/2009 | Manaresi et al. |
| 2009/0288963 A1* | 11/2009 | Guerrieri ............. B03C 5/005 205/792 |
| 2010/0035292 A1 | 2/2010 | Levhenko et al. |
| 2010/0043575 A1 | 2/2010 | Tajima |
| 2010/0248285 A1 | 9/2010 | Manaresi |
| 2010/0331205 A1 | 12/2010 | Medoro |
| 2011/0003380 A1 | 1/2011 | Miltenyi et al. |
| 2011/0183433 A1 | 7/2011 | Motadel et al. |
| 2011/0193006 A1 | 8/2011 | Simone et al. |
| 2012/0071335 A1 | 3/2012 | Manaresi et al. |
| 2012/0091001 A1 | 4/2012 | Manaresi et al. |
| 2012/0184010 A1 | 7/2012 | Medoro et al. |
| 2013/0118903 A1 | 5/2013 | Becker et al. |
| 2014/0131207 A1 | 5/2014 | Medoro et al. |
| 2014/0302490 A1 | 10/2014 | Medoro et al. |
| 2014/0315236 A1 | 10/2014 | Manaresi |
| 2015/0031040 A1 | 1/2015 | Calanca et al. |
| 2016/0202173 A1 | 7/2016 | Medoro et al. |
| 2017/0136464 A1 | 5/2017 | Manaresi |

FOREIGN PATENT DOCUMENTS

| | | |
|---|---|---|
| DE | 19500660 B4 | 12/2007 |
| EP | 0 500 727 A1 | 9/1992 |
| EP | 1145766 B1 | 8/2007 |
| EP | 1304388 B1 | 2/2008 |
| EP | 1179585 B1 | 7/2008 |
| EP | 2260943 A1 | 12/2010 |
| JP | 58211272 A | 12/1983 |
| JP | 2000292480 A | 10/2000 |
| JP | 2002503334 A | 1/2002 |
| JP | 2002311461 A | 10/2002 |
| JP | 2002536167 A | 10/2002 |
| JP | 2003121886 A | 4/2003 |
| JP | 2003202604 A | 7/2003 |
| JP | 2004000935 A | 1/2004 |
| JP | 2005501296 A | 1/2005 |
| JP | 2005507997 A | 3/2005 |
| JP | 2005510705 A | 4/2005 |
| JP | 2005176836 A | 7/2005 |
| JP | 2005257283 A | 9/2005 |
| JP | 2005304445 A | 11/2005 |
| JP | 2006504974 A | 2/2006 |
| JP | 2006512092 A | 4/2006 |
| JP | 2006517024 A | 7/2006 |
| JP | 2007017163 A | 1/2007 |
| JP | 2008533487 A | 8/2008 |
| JP | 60071935 | 4/2015 |
| WO | WO-91/07660 A1 | 5/1991 |
| WO | WO-91/08284 A1 | 6/1991 |
| WO | WO-98/04355 A1 | 2/1998 |
| WO | WO-99/17883 A1 | 4/1999 |
| WO | WO-00/28313 A1 | 5/2000 |
| WO | WO-00/47322 A2 | 8/2000 |
| WO | WO-00/69525 A1 | 11/2000 |
| WO | WO-00/69565 A1 | 11/2000 |
| WO | WO-01/11340 A1 | 2/2001 |
| WO | WO-01/21311 A1 | 3/2001 |
| WO | WO-02/12896 A1 | 2/2002 |
| WO | WO-02/41999 A1 | 5/2002 |
| WO | WO-02/088702 A2 | 11/2002 |
| WO | WO-03/014739 A1 | 2/2003 |
| WO | WO-03/035895 A2 | 5/2003 |
| WO | WO-03/045556 A2 | 6/2003 |
| WO | WO-2004/030820 A2 | 4/2004 |
| WO | WO-2004/071668 A1 | 8/2004 |
| WO | WO-2005/060432 A2 | 7/2005 |
| WO | WO-2005/098395 A1 | 10/2005 |
| WO | WO-2006/003214 A2 | 1/2006 |
| WO | WO-2006008602 A2 | 1/2006 |
| WO | WO-2006/018849 A2 | 2/2006 |
| WO | WO-2007/010367 A2 | 1/2007 |
| WO | WO-2007/049103 A1 | 5/2007 |
| WO | WO-2007049120 A2 | 5/2007 |
| WO | WO-2007/110739 A2 | 10/2007 |
| WO | WO-2007/116312 A2 | 10/2007 |
| WO | WO-2007/147018 A1 | 12/2007 |
| WO | WO-2007147076 A2 | 12/2007 |
| WO | WO-2008/112274 A2 | 9/2008 |
| WO | WO-2008/131035 A2 | 10/2008 |
| WO | WO-2009/022222 A2 | 2/2009 |
| WO | WO-2010/106426 A1 | 9/2010 |
| WO | WO-2010/106434 A1 | 9/2010 |
| WO | WO-2010/149292 A1 | 12/2010 |

OTHER PUBLICATIONS

Cheung et al., Impedance spectroscopy flow cytometry: on-chip label-free cell differentiation, Cytometry Part A, 65A(2):124-32 (2005).

De Bono et al., Circulating tumor cells predict survival benefit from treatment in metastatic castration-resistant prostate cancer, Clin. Cancer Res., 14(19):6302-9 (2008).

Diamond et al., Flow cytometry in the diagnosis and classification of malignant lymphome and leukemia, Cancer, 50:1122-35 (1982).

English translation of Office Action, Japanese patent application No. 2012-167396 (dated Aug. 2, 2013).

(56) References Cited

OTHER PUBLICATIONS

Fiedler et al., Dielectrophoretic sorting of particles and cells in a microsystem, Anal. Chem., 80(9):1909-15 (1998).

Fiedler et al., Electrocasting formation and structuring of suspended microbodies using A.C. generated field cages, Microsystem Technologies, Berlin, Germany, pp. 1-7 (Dec. 1, 1995).

Final office action, U.S. Appl. No. 11/724,697, dated Jan. 27, 2012.

Final office action, U.S. Appl. No. 12/091,367, dated Nov. 1, 2011.

Fuchs et al., Electronic sorting and recovery of single live cells from microlitre sized samples, Lab Chip, 6:121-6 (2006).

Fuhr et al., Positioning and manipulation of cells and microparticles using miniturized electric field traps and travelling waves, Sensors and Materials, 7(2):131-46 (1995).

Gascoyne et al., Dielectrophoresis-based programmable fluidic processors, Lab Chip, 4:299-304 (2004).

Gascoyne et al., Particle separation by dielectrophoresis, Electrophoresis, 23(13): 1973-83 (2002).

Green et al., Ac Electrokinetics: a survey of sub-micrometre particle dynamics, J. Phys. D: Appl. Phys., 33:632-41 (Dec. 10, 1999).

Hughes, Strategies for dielectrophoretic separation in laboratory-on-a-chip systems, Electrophoresis, 23(16): 2569-82 (2002).

Ince et al., Association of k-ras, b-raf, and p53 status with the treatment effect of bevacizumab, J. Natl. Cancer Inst., 97(13):981-9 (2005).

International Preliminary Report on Patentability for corresponding International Application No. PCT/EP2005/053235, dated Jan. 9, 2007.

International Preliminary Report on Patentability for PCT/IB2012/057797, dated Jul. 1, 2014.

International Preliminary Report on Patentability for corresponding International Application No. PCT/IB2009/007316, dated Jan. 21, 2011.

International Preliminary Report on Patentability for PCT/IB2006/000636, dated Apr. 29, 2008.

International Preliminary Report on Patentability for PCT/IB2006/001984, dated Dec. 3, 2007.

International Preliminary Report on Patentability for PCT/IB2006/002965, dated Apr. 29, 2008.

International Preliminary Report on Patentability for PCT/IB2007/000751, dated Sep. 30, 2008.

International Preliminary Report on Patentability for PCT/IB2008/002873, dated May 4, 2010.

International Preliminary Report on Patentability for PCT/IB2010/000615, dated Sep. 20, 2011.

International Preliminary Report on Patentability for PCT/IB2012/055981, dated Apr. 29, 2014.

International Search Report and Written Opinion for corresponding International Application No. PCT/EP2005/053235, dated May 2, 2006.

International Search Report and Written Opinion for corresponding International Application No. PCT/IB2009/007316, dated Feb. 3, 2010.

International Search Report and Written Opinion for PCT/IB2006/000636, dated Sep. 8, 2006.

International Search Report and Written Opinion for PCT/IB2006/001984, dated Feb. 27, 2007.

International Search Report and Written Opinion for PCT/IB2006/002965, dated Jun. 15, 2007.

International Search Report and Written Opinion for PCT/IB2007/000751, dated Nov. 16, 2007.

International Search Report and Written Opinion for PCT/IB2010/000615, dated Aug. 26, 2010.

International Search Report and Written Opinion for PCT/IB2012/055981, dated Jan. 22, 2013.

International Search Report in PCT/IB2008/001083 dated Oct. 28, 2008.

International Search Report in PCT/IB2009/007010, dated Jan. 8, 2010.

International Search Report in PCT/IB2008/002873, dated Aug. 3, 2009.

Jones, An electromechanical interpretation of electrowetting, J. Micromech. Microeng., 15(6):1184-7 (2005).

Klein et al., Comparative genomic hybridization, loss of heterozygosity, and DNA sequence analysis of single cells, Proc. Natl. Acad. Sci. USA, 96(8):4494-9 (1999).

Leers et al., Immunocytochemical detection and mapping of a cytokeratin 18 neo-epitope exposed during early apoptosis, J. Pathol., 187(5):567-72 (1999).

Long et al., A new preprocessing approach for cell recognition, IEEE Trans. Information Tech. Biomed., 9(3):407-12 (2005).

Manaresi et al., A CMOS chip for individual cell manipulation and detection, IEEE J. Solid-State Circuits, 38:2297-305 (2003).

Medoro et al., A lab-on-a-chip for cell detection and manipulation, IEEE Sensors Journal, 3(3):317-25 (2003).

Medoro et al., A lab-on-a-chip for cell separation based on the moving-cages approach, Proceedings of the 16th Conference on Solid State Transducers, pp. 500-501 (Sep. 15, 2002).

Medoro et al., Dielectrophoretic cage-speed separation of bio-particles, Sensors, Proceedings of the IEEE Vienna, Austria, Oct. 24-27, 2004, pp. 76-79.

Milner et al., Dielectrophoretic classification of bacteria using differential impedance measurements, Electronics Letters, 34(1):66-8 (1998).

Nagrath et al., Isolation of rare circulating tumour cells in cancer patients by microchip technology, Nature, 450(7173):1235-9 (2007).

Nieuwenhuis et al., Near-field optical sensors for particle shape measurements, Sensors Journal IEEE, 3(5):646-51 (2003).

Nonfinal office action, U.S. Appl. No. 11/724,697, dated Jun. 7, 2011.

Nonfinal office action, U.S. Appl. No. 11/724,697, dated Sep. 23, 2010.

Nonfinal office action, U.S. Appl. No. 11/996,068, dated Jan. 4, 2013.

Nonfinal office action, U.S. Appl. No. 12/091,367, dated Mar. 25, 2011.

Nonfinal office action, U.S. Appl. No. 12/091,438, dated Jul. 25, 2013.

Nonfinal office action, U.S. Appl. No. 12/294,860, dated Jan. 27, 2012.

Nonfinal office action, U.S. Appl. No. 12/740,170, dated Jun. 5, 2013.

O'Hara et al., Ratcheting electrophoresis microchip (REM) for programmable transport and separation of macromolecules, Proceedings of the International Mechanical Engineering Congress and Exposition, 3:619-28 (2001).

Office Action, Japanese patent application No. 2011-535174, dated Nov. 19, 2013.

Office Action, U.S. Appl. No. 11/724,697, dated Jan. 27, 2012.

Ohta et al., Tech. Dig. of the Solid State Sensor, Actuator and Microsystems, Workshop, pp. 216-219 (2004).

Petersson et al., Carrier medium exchange through ultrasonic particle switching in microfluidic channels, Anal. Chem., 77:1216-21 (2005).

Pethig et al., Enhancing traveling-wave dielectrophoresis with signal superposition, IEEE Eng. Med. Biol. Mag., 22(6):43-50 (2003).

Reichle et al., Combined laser tweezers and dielectric field cage for the analysis of receptor-ligand interactions on single cells, Electrophoresis, 22(2):272-82 (2001).

Romani et al., Capacitive sensor array for localization of bioparticles in CMOS lab-on-a-chip, Proc. Int. Solid State Circuit Conference, 1:224-5 (2004).

Rousselet et al., Directional motion of brownian particles induced by a periodic asymmetric potential, Nature, 370(6489):446-8 (1994).

Schnelle et al., Three-dimensional electric field traps for manipulation of cells—calculation and experimental verfication, Biochem. Biophys. Acta, 1157(2):127-40 (1993).

Stoecklein et al., Direct genetic analysis of single disseminated cancer cells for prediction of outcome and therapy selection in esophageal cancer, Cancer Cell, 13:441-53 (2008).

Suehiro, The dielectrophoretic movement and positioning of a biological cell using a three-dimensional grid electrode system, J. Phys. D: Appl. Phys., 31:3298-305 (1998).

(56) References Cited

OTHER PUBLICATIONS

Zieglschmid et al., Detection of disseminated tumor cells in peripheral blood, Crit. Rev. Clin. Lab. Sci., 42(2):155-96 (2005).
Vona et al., Isolation by size of epithelial tumor cells : a new method for the immunomorphological and molecular characterization of circulatingtumor cells, Am. J. Pathol., 156(1):57-63 (2000).
Examination Report, for corresponding European Patent Application No. 08844732.1 dated Dec. 12, 2016.
Voldman et al., "Engineered system for the physical manipulation of single cells" Current Opinion in Biotechnology, London, GB. vol. 17, No. 5, Oct. 1, 2006, pp. 532-537.

* cited by examiner

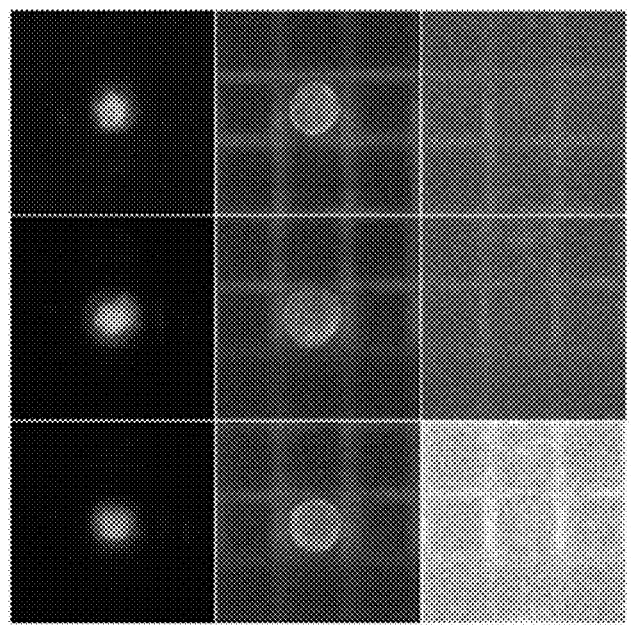
FIG. 3A - TUMOUR CELLS (DAPI +, EpCAM-FITC +, CD45-PE -)
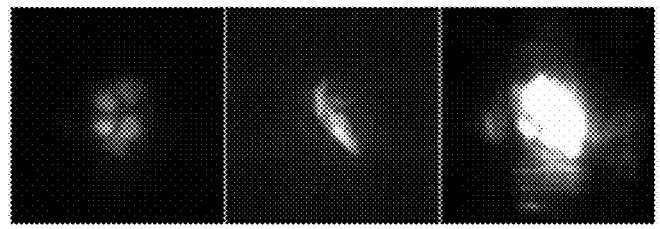
FIG. 3B - SPURIOUS CELLS (DAPI+, EpCAM-FITC +, CD45-PE +)
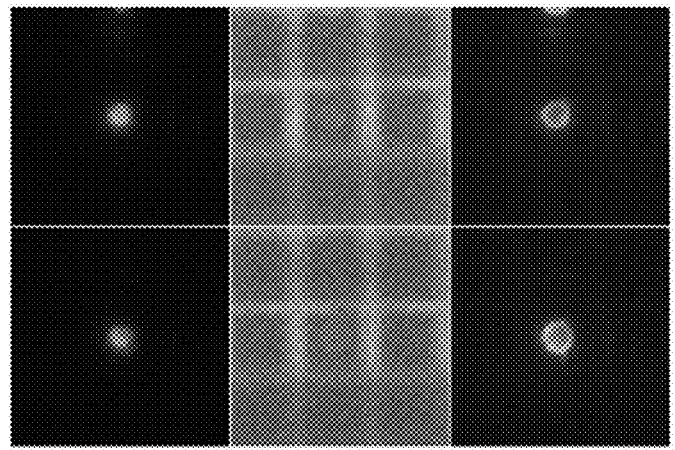
FIG. 3C - LYMPHOCYTES (DAPI+, EpCAM-FITC -, CD45-PE +)

FIG. 16

| | Mixed | Tumor | | | | Stromal | |
|---|---|---|---|---|---|---|---|
| | SG-TC gDNA:AmpDNA 10ng L07 | TC 085-DA L19 | 300-DA L20 | 300-DA L12 | 300-DA L15 | 300-DA L21 | 600-DA L13 | SC 085-DA L16 | SC 300-DA L17 |
| Gene ID | Position | Allele Name | Freq | Freq | Freq | Freq | Freq | Freq | Freq | Freq | Freq | | | | | | | | |
| | 149,433,596 | --- | 100,0 | 100,0 | 100,0 | 100,0 | 100,0 | 100,0 | 100,0 | 100,0 | Germline Homozygous |
| | 1,807,894 | --- | 100,0 | 100,0 | 100,0 | 100,0 | 100,0 | 100,0 | 100,0 | 100,0 | Germline Homozygous |
| | 55,141,055 | --- | 100,0 | 100,0 | 100,0 | 100,0 | 100,0 | 100,0 | 100,0 | 100,0 | Germline Homozygous |
| | 112,175,770 | --- | 98,4 | 100,0 | 100,0 | 100,0 | 100,0 | 100,0 | 98,6 | 100,0 | Germline Homozygous |
| | 149,433,597 | --- | 98,2 | 100,0 | 100,0 | 100,0 | 99,7 | 98,9 | 98,5 | 100,0 | Germline Homozygous |
| | 7,578,461 | COSM10670 | 17,3 | 22,1 | 18,3 | 8,1 | 8,4 | 95,3 | 3,8 | 82,6 | 57,1 | Tumor LoH on WT Germline Het |
| | 7,579,472 | --- | 65,4 | 73,2 | 55,7 | 88,8 | 78,4 | 93,2 | 72,6 | 42,0 | 33,0 | Tumor LoH on WT Germline Het |
| | 55,980,239 | --- | 20,1 | 15,1 | 80,1 | 46,3 | 57,6 | 80,9 | 85,0 | 48,6 | 36,1 | Tumor LoH on Var Germline Het |
| | 55,962,546 | --- | 15,3 | 10,3 | 86,7 | 27,0 | 28,9 | 23,6 | 44,5 | 37,5 | 49,9 | Tumor LoH on Var Germline Het |
| | 48,586,344 | --- | 41,3 | 39,0 | 60,1 | 26,6 | 23,8 | 20,8 | 22,0 | 41,8 | 36,1 | Tumor Copy+ on Var Germline Het |
| | 55,249,063 | --- | 59,3 | 38,6 | 40,4 | 47,9 | 57,6 | | 27,7 | 40,8 | 53,4 | Tumor Copy+ on Var Germline Het |
| | 116,339,642 | COSM706 | 57,0 | 59,0 | | | | | | 36,6 | 44,4 | Germline Heterozygous |
| | 28,610,183 | --- | 42,6 | 40,4 | 12,7 | | | | | 51,1 | 35,1 | Tumor Copy+ on WT Germline Het |
| | 43,615,633 | --- | 40,1 | 39,0 | 16,8 | 22,8 | 23,8 | | | 53,9 | 51,9 | Tumor Copy+ on WT Germline Het |
| | 43,613,843 | --- | 39,9 | 36,8 | | 39,4 | | | | | | |
| | 55,972,974 | --- | 6,1 | 4,6 | | 6,8 | 5,6 | 5,5 | 5,0 | 11,3 | 18,8 | Subpopulation in stromal |
| | 10,183,852 | --- | 4,5 | 9,0 | 6,2 | | 4,4 | 4,8 | | 6,7 | | False Positives |
| | 112,176,035 | --- | --- | --- | | | | | | 6,8 | 5,9 | False Positives |

FIG. 17

SEQUENCE LISTING

<160> NUMBER OF SEQ ID NOS: 2

<210> SEQ ID NO 1
<211> LENGTH: 34
<212> TYPE: DNA
<213> ORGANISM: Homo sapiens

<400> SEQUENCE: 1
ggtagttgga gctgttggcg taggcaagag tgcc          34

<210> SEQ ID NO 2
<211> LENGTH: 25
<212> TYPE: DNA
<213> ORGANISM: Homo sapiens

<400> SEQUENCE: 2
agttggagct ggtggcgtag gcaag          25

METHOD FOR IDENTIFICATION, SELECTION AND ANALYSIS OF TUMOUR CELLS

CROSS-REFERENCE TO RELATED APPLICATION

This is a continuation-in-part of U.S. patent application Ser. No. 13/127,640, which is a U.S. national stage application of International Patent Application No. PCT/IB2009/007316 filed on Nov. 4, 2009, which in turn claims the benefit of Italian Patent Application No. TO2008A000814, filed Nov. 4, 2008, the respective disclosures of which are each incorporated herein by reference in their entireties.

BACKGROUND

1. Field of the Art

The present invention relates, in general, to diagnostic methods based upon identification, isolation, and subsequent analysis of tumour cells. In particular, the invention relates to diagnostic methods that find application in the oncology sector, and that hence involve identification and isolation of circulating tumour cells (CTCs) or disseminated tumour cells (DTCs) or tumour cells from very small samples.

2. State of the Art

The diagnosis of numerous pathological conditions, in particular that of tumours, is typically performed according to methods characterized, on the one hand, by different degrees of invasiveness and, on the other, by different levels of performance in terms of specificity, sensitivity, and reliability.

Some methods of screening are based upon analyses aimed at detecting the presence of biomarkers in the peripheral bloodflow (for example, CA-125, CEA, PSA) or in other biological fluids (for example, test of occult blood in the faeces or test on faecal DNA). Said methods, however, are based upon an indirect evaluation that is a function of the concentration of a biomarker and not on the direct analysis, for example, of tumoural tissue. Consequently, their sensitivity and specificity are not particularly high.

In the case, considered by way of example, of prostate cancer, one of the most widespread forms of cancer in the male population (approximately one quarter of all the cases of cancer, 300,000 new cases a year in Europe), screening on the basis of serological parameters (dosages of PSA) is widespread, but has a poor sensitivity and specificity.

More invasive procedures, such as digital rectal examination can at times complete the clinical picture, but more frequently it is necessary to carry out a prostatic biopsy to have a more accurate diagnosis, in an escalation of invasiveness that results in a growing discomfort for the patient and in non-negligible costs for the health system.

Similar situations arise in other contexts, such as cancer of the colon-rectum, where recourse is frequently had to the evaluation of occult blood in the faeces, or else an invasive analysis is performed via colonscopy and, possibly, a biopsy with sampling of tissues taken directly from the colon-rectum.

Since, in this context, early diagnosis enables on average a more effective treatment, it is obviously of interest to evaluate the onset of cancer at an early stage and with a high degree of sensitivity and specificity.

In this sense, recent studies (for example, Zieglschmid et al., *Crit. Rev. Clin. Lab. Sci.* 42, 155-196 (2005)) on circulating tumour cells (CTCs) have demonstrated that, in the peripheral bloodflow, cells deriving from the primary tumour are found. Even though they are extremely rare, the possibility of identifying them and isolating them constitutes a potentially very interesting alternative to the invasive methods described previously for obtaining specimens of tumoural tissue to be characterized, subsequently, for diagnostic purposes. Regulatory bodies, such as the FDA, have already approved some systems for clinical use based upon CTCs for evaluation of patients presenting metastases.

For the majority of patients affected by a cancer, in fact, it is not the main tumour that causes death in so far as, if identified at a sufficiently early stage, it can be eliminated surgically, by means of radiotherapy, chemotherapy, or by a combination of said methods. Instead, the most frequent cause of death are metastases, i.e., tumoural colonies originated by malignant cells that detach from the main tumour and migrate towards other districts of the body, even at a considerable distance from the main tumoural site. Since they are difficult to identify and eliminate, it is frequently impossible to treat all the metastases successfully. Consequently, from the clinical standpoint their formation can be considered the conclusive event in the natural progress of a cancer.

Consequently, since there has been demonstrated, in the case of breast cancer, cancer of the colon, and cancer of the prostate, a correlation between the number of CTCs and the increased risk of unfavourable outcome of the illness, it appears evident that the possibility of isolating them and, by means of molecular analysis, obtaining a complete informative picture therefrom having clinical importance, would have very significant diagnostic repercussions.

It has moreover been proven that the analysis of disseminated tumour cells (DTCs), i.e., of tumour cells that can be found in the bone marrow or in the lymph nodes, is, in certain contexts, even more significant than the analysis of the primary tumour. Some research groups, for example, have noted (Klein et al., *Tumour cell.* 13(5), 441-53 (2008)) that the over-expression of HER2, which can be detected in a single DTC but not in the primary tumour, proves predictive of a very high risk of death.

Furthermore, it is known, for example from the patent No. EP1109938, that the analysis of single multiple cells can be more informative as compared to the analysis of a set of cells. In particular, it has been found (Klein et. al., *Proc. Natnl. Acad. Sci. USA* 96, 4494-4499 (1999)) that different DTCs of one and the same patient have different chromosome variations (losses and amplifications in different sites).

At the current state of the art, for isolation of circulating and disseminated tumour cells there are, however, available approaches of a chiefly analytical nature that are very complex and laborious, which, however, have limited yields and generate specimens distinguished by a low degree of purity. Consequently, said specimens of CTCs or DTCs are not compatible with some of the most refined and reliable diagnostic procedures, such as sequencing. The limited purity, in fact, determines a high risk of false positives and false negatives caused by wrong calls in the bases of the sequence.

Attempts have been made (Nagrath et al., *Nature*, 450, 1235-1241 (2007)) to isolate CTCs by means of microfluidic devices with an inner surface coated with anti-EpCAM antibodies (expressed in epithelial cells but not in leukocytes) that are able to process volumes of blood of the order of millilitres, without having to resort to preliminary treatments that entail operations with a high risk of loss of part of the cells of interest (for example, centrifugation, flushing and incubation). However, said methods have led to levels of purity on average of 50%-60%, which do not prove sufficient for carrying out, downstream, analyses for which the purity of the specimen is crucial, such as, for example, the evaluation of copy-number variations, microsatellite instability, loss of heterozygosity (LoH), gene expression in which a better signal-to-noise (S/N) ratio is fundamental for diagnostic applications, or identification of new drugs, or again in the sector of research into cancer-initiating cells.

The problems encountered with molecular analyses on low purity samples of CTCs are the same that arise when only small samples of solid tumours are available. Preparing samples enriched with tumor cells for molecular analysis can be challenging. Factors affecting biomarker analyses include the tissue-preparation process, and the initial size, quality, and composition of the biopsy specimen. While fixation of tissue with formalin and embedding in paraffin (FFPE) has become standard practice for pathology laboratories, fixation and extraction processes can change the molecular composition of the specimen in significant ways. DNA extraction methods do not discriminate genomic content of tumor cells from that of stromal cells, so the accuracy of any biomarker assay is dependent on the selection of tissue sections bearing an adequate representation of tumor cells. For many tumors, finding suitable tissue sections with sufficient tumor cells, or tissue not impaired by the presence of necrotic or damaged cells, can be difficult. Tumor cells within biopsies are molecularly heterogeneous, consisting of both cancerous cells and an indeterminate number of normal cells. Such composition can result in equivocal or inconclusive test results that may ultimately disqualify patients for certain therapies or confound biomarker analyses in clinical studies. Hence, any method developed to improve on standard DNA extraction methods by enriching for specific target cells must also work effectively with miniscule FFPE sections as starting sample material.

Corver W E et al. (J Pathol, 206, 233-241 (2005)) reports a multiparameter DNA flow cytometric method enabling the detection of neoplastic and stromal cells in sample from FFPE tissues. The method involves an initial procedure in which the FFPE tissue is deparaffinised and cells are dissociated with a 1% dispase/1% collagenase solution. The cell suspension obtained thereby is then stained for keratin (FITC), vimentin (R-PE) and DNA (PI) and then subjected to flow cytometric analysis. The drawbacks of this method are however that, very often, cells recovered from FFPE samples are too little in number to perform a FACS analysis, and that separations are incomplete, producing partially enriched rather than pure, separate population of tumour and normal cells.

Similar considerations can be extended to other methods the enormous diagnostic potential of which has been highlighted, which, however, cannot be concretely implemented since the known procedures of enrichment of biological specimens and isolation of a population of rare cells therein do not enable sufficient levels of purity to be obtained, if not following upon a heavy, complex and costly analytical workload that cannot, consequently, find application in medical practice. For instance (Bonci et al. "The miR-15a-miR-16-1 cluster controls prostate cancer by targeting multiple oncogenic activities" Oct. 19, 2008; doi:10.1038/nm.1880), incorporated herein for mere reference as regards the relevant parts, it has recently been demonstrated that some microRNAs (miRNAs), i.e., short single-strand non-encoding fragments of RNA, containing approximately 22 nucleotides, are directly involved in the development and progress of cancer. From a study of the expression of miR-15a and miR-16 in cells of a primary tumour (prostate cancer) by means of quantitative PCR, there has been noted a considerable under-regulation of both of the miRNAs as compared to the corresponding healthy tissue. Said datum has been confirmed by means of in-situ hybridization (ISH). It has moreover been demonstrated that the deletion of the miR-15a-miR-16 cluster is generally associated to advanced stages of the illness, even though in some cases the under-regulation of these miRNAs has been recorded already during the initial stages of the development of cancer. Consequently, from the diagnostic standpoint, the possibility of isolating tumour cells and of evaluating whether they present an under-regulation of these miRNAs would provide a precise indication on the state of advance of the illness, which is useful to the physician also for the choice of the most appropriate form of therapy.

To proceed with further considerations of a therapeutic nature, it is worthwhile recalling that some therapeutic approaches in the oncology sector are based upon the use of monoclonal antibodies that are able to have a direct influence upon the survival of tumour cells, depriving them of essential signals of extracellular proliferation, such as those mediated by growth factors through their cell receptors. For example, one of the targets of interest, in this context, is the epidermal-growth-factor receptor (EGFr). Binding between the epidermal growth factor (EGF) and the corresponding receptor EGFr triggers a cascade of cellular biochemical events, which include autophosphorylation and internalization of EGFr, which culminates in cell proliferation.

It has been shown that both EGF and the transforming growth factor-α (TGF-α) bind to EGFr and lead to cell proliferation and growth of the tumour. In many cases, the increased expression of EGFr has been accompanied by the production of TGF-α or EGF by the tumour cells, thus suggesting involvement of an autocrine growth control in the progress of cancer. Consequently, there has been proposed the use of antibodies against EGF, TGF-α and EGFr in the treatment of tumours in which they are expressed or over-expressed. It has recently been demonstrated, as described in the international patent application published under No. WO28112274, the presence of a mutation of which in the K-RAS gene or in the B-RAF gene in tumour cells constitutes an indication on the fact that the tumour will not respond to the treatment with an agent designed to bind to a polypeptide of EGFr.

It will be understood that the possibility of detecting, starting from a specimen of tumour cells taken from a patient by means of a non-invasive procedure, the presence of such a mutation would provide the physician with a tool of enormous importance for evaluating whether to proceed with a therapy based upon the use of an anti-EGFr monoclonal antibody or else reject it, knowing beforehand that it would not be effective.

Also in this perspective, however, the methodologies of enrichment, identification and isolation of rare cells in the blood, in other biological fluids, in small biopsies and in FFPE tissue samples, do not enable a sufficient purity to be obtained to guarantee that the subsequent analysis will be reliable (exclusion of false positives, false negatives, etc.) and, in some cases, that they can even materially be conducted (for example, for the cases in which, since the purity is low, the signal-to-noise ratio is too low to obtain a valid reading).

SUMMARY OF THE INVENTION

Consequently, an aim of the present invention is to provide a method for identification, isolation, and subsequent analysis of tumour cells that will overcome the drawbacks of the known art described previously.

Consequently, provided according to the present invention are procedures for diagnostic purposes to be carried out on a purified specimen of cells of interest obtained starting from a sample taken from a patient, which are identified and subsequently isolated until a purity of at least 90% is obtained, operating according to the method specified in claim 1.

Preferably, the purified specimen has a purity of at least 95%. Even more preferably, purified specimen has a purity of 100%. In this context, by the term "purity" of a purified sample there is intended the percentage of cells of interest with respect to total cells in the purified sample. By way of example, considering that tumour cells are the cells of interest, if a purified sample contains 9 tumour cells and 1 normal cell, the purified sample will have a purity of 90%. If, instead, the sample contains 2 cells and both cells are tumour cells, the purified sample will have a purity of 100%.

In particular, according to a preferential embodiment of the present invention the step of obtaining a purified sample of tumour cells is performed according to a technology developed by the present applicant and based upon the use of a silicon microchip that integrates several hundreds of thousands of electrodes of micrometric dimensions by manipulating individual cells so as to isolate the cells of interest with a unitary purity rendering them available for molecular analysis. In this way, the method according to the invention provides cells with a high purity, is highly automated for the most delicate part of the process (isolation of individual cells), and enables implementation of analytical techniques of high diagnostic and predictive reliability. In the light of what has been described previously, there will emerge clearly the innovative scope, at a diagnostic and therapeutic level, of the present invention, which enables improvement of the oncological treatment in the different stages of the course of the illness, rendering possible both a non-invasive early diagnosis having a level of reliability comparable with a biopsy, and a sensitive and accurate follow-up in the course of the treatment with specific cancer drugs and/or in the post-operative stage in order to follow the evolution of the illness and the quality of the response to the clinical treatments, both in the metastatic stage and in the adjuvant stage.

According to the present invention, a sample is obtained from a patient.

The sample may be an organic fluid taken in a non-invasive manner from a patient and is, in a first instance, processed by making one or more passages of enrichment of the cells of interest according to one or more methodologies known in the art, such as Ficoll, selective lysis of the erythrocytes, filtration with filters based upon dimension of the cells—obtained by means of photolithographic micromachining or other technique, such as track-etched membranes, depletion or magnetic enrichment. The enriched cells are then labelled with specific antibodies for identifying the cells of interest and/or the contaminating cells, etc.

In this context, by the expression "organic fluid" or "corporeal fluid" reference is made to a fluid obtained starting from a corporeal specimen in which there is a high probability of finding cells of interest. The organic fluid can be obtained from the corporeal specimen, either directly—such as for example, peripheral bloodflow, bone marrow, urine—or indirectly, such as for example, by means of trypsinization of a tissue from a lymph node.

In this context, by the expression "cells of interest" reference is made to cells, the characteristics of which, detectable by means of appropriate techniques of analysis, can provide indications of a diagnostic or therapeutic nature on a pathological condition of the patient.

For instance, the corporeal fluid is peripheral blood, which can be drawn in a substantially non-invasive way from the patient, according to the methodologies commonly in use, and the cells of interest are circulating tumour cells (CTCs).

As further example, the organic fluid is blood from bone marrow, and the cells of interest are disseminated tumour cells (DTC).

As an alternative, the sample may be a tumour biopsy or a formalin fixed and paraffin embedded (FFPE) tumour biopsy. The biopsy is, in a first instance, processed so as to obtain a suspension of cells in a fluid. In the case of a FFPE tumour biopsy, the suspension of cells is obtained by first subjecting the FFPE biopsy sample to deparaffinization and then dissociating single cells of the FFPE biopsy sample with a 1% dispase/1% collagenase 1a solution. Such a methodology is known from Corver W E et al. (J Pathol, 206, 233-241 (2005). The suspended cells are then labelled with specific antibodies for identifying the cells of interest and/or the contaminating cells, etc.

The method of the invention is then characterized by the use of a microfluidic system that is able to individually select single cells from the enriched sample/suspension of cells and isolate them in an automatic or semi-automatic non-manual way.

Used hereinafter for reasons of simplicity is the term "single cells" or "individual cells", but this term must be understood as including a single cell or a single aggregate of cells in so far as, in general, it may occur that the cells of interest present as not isolated but bound to one or more other cells, whether tumour cells or non-tumour cells. Furthermore, there must be understood also the possibility of analysing portions of cells, such as isolated nuclei.

Via said isolation of the cells in the microfluidic system, a set is obtained containing only cells of interest, i.e., a specimen of a purity equal to 100%, which thus proves suitable for being subjected to a plurality of procedures of molecular analysis.

Advantageously, in the aforesaid microfluidic system for the individual selection of single cells, the selection is made on the basis of images of the cells themselves.

Advantageously, said images of the cells are acquired in the absence of flow in the medium of suspension of the cells themselves.

Advantageously, said images comprise images acquired in fluorescence.

By "microfluidic device" is understood, herein, a device designed to manage volumes of liquid in a laminar-flow regime, in which the space for containing the liquid during analysis has at least one dimension smaller than 1 mm.

By "device capable of individually selecting single cells" is here understood a device that is able to carry out selection of one or more single cells, one at a time or simultaneously, on the basis of parameters evaluated individually on each cell.

By "non-manual isolation" is understood a movement of the cells in which manuality of the operator is not required, such as for example, in the case of movement by means of mobile dielectrophoretic cages.

By "automatic isolation" is understood a movement of the cells in which intervention of the operator is not required, such as for example, in the case of movement by means of dielectrophoretic cages managed by a program executed in a substantially non-interactive way by a microprocessor.

By "semi-automatic isolation" is understood a movement of the cells in which the interaction with the operator enables exerting an indirect control on the manipulation, such as for example, in the case of movement, for example by means of dielectrophoretic cages, managed by an interactive program executed by a microprocessor.

Advantageously, the aforesaid selection is made in an automatic or semi-automatic way.

By "automatic selection" is understood herein a selection of the cells in which intervention of judgement of the operator is not required, such as for example, in the case where there is determined automatically with an automatic classifier which cells correspond effectively to tumour cells of interest. For example, this could be performed with a classifier of images that processes the acquired images of the cells, extracts the discriminating features therefrom and classifies them on the basis of an algorithm.

By "semi-automatic selection" is understood herein a selection of the cells in which intervention of judgement of the operator is required. For instance, this could be performed with a system that acquires the images of the cells, extracts the discriminating features therefrom, and proposes them to the operator for the final decision as to whether they should be selected.

The molecular analysis on the cells recovered can then be executed via different techniques—thanks to the high purity of the specimen recovered—, amongst which, by way of non-limiting example:
- sequencing (for example, for identification of mutations);
- microsatellite analysis (for example, with Quantitative Fluorescent PCR, i.e., QF-PCR);
- comparative genomic hybridization (CGH);
- array CGH;
- end-point PCR;
- real-time PCR;
- methylation analysis:
    - quantitative methylation analysis with pyrosequencing;
    - bisulphite-genomic-sequencing PCR (BSP);
    - methylation-specific PCR (MSP);
    - Combined Bisulphite Restriction Analysis of DNA (COBRA)
    - methylation-sensitive single-nucleotide primer extension (MS-SNuPE)
- analysis of gene expression;
- RT-PCR;
- single-cell gene expression;
- digital PCR.

Further characteristics and advantages of the invention will emerge clearly from the ensuing description of some non-limiting examples of embodiment thereof, provided with reference to the figures of the annexed drawings.

BRIEF DESCRIPTION OF THE FIGURES

FIGS. 3A, 3B and 3C show images acquired in the course of scanning of circulating tumour cells according to the method of the invention;

FIG. 10 shows circulating tumour cells according to the method of the invention and FIGS. 8 and 9 the corresponding negative controls (normal leukocytes).

FIG. 11C shows the analysis of DAPI content of tumour and stromal cells obtained with the DEPArray® for the sample of FIG. 11a.

FIG. 16 shows a table of frequencies of mutations found respectively in mixed cell preparations, and in tumour and stromal cells sorted by DEPArray™.

FIG. 17 shows a table summarizing frequencies of mutations found in different population of cells sorted from a lung cancer patient FFPE sample.

DETAILED DESCRIPTION

Figure 1:
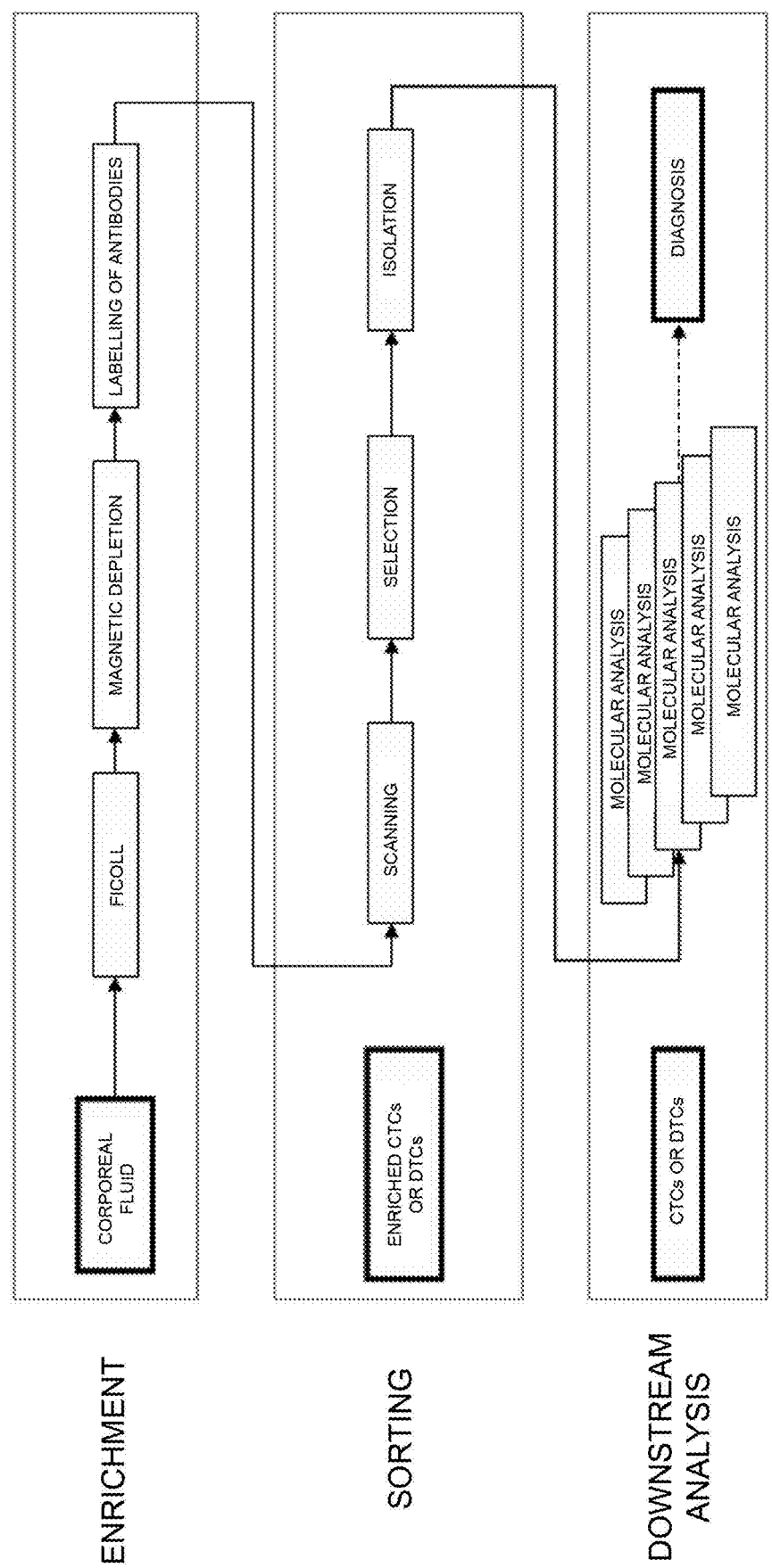
FIG. 1 shows a flowchart summarizing an embodiment of a non-invasive method of diagnosis according to the present invention.

The subject of the present invention is a method of identification, isolation, and subsequent analysis of tumour cells. In a first embodiment, the tumour cells are rare cells, in particular circulating tumour cells or disseminated tumour cells, obtained preferably by means of a sampling of a non-invasive nature. In a second embodiment, the tumour cells are obtained from formalin-fixed paraffin embedded samples.

First Embodiment

Circulating Tumour Cells or Disseminated Tumour Cells

Sampling

The samples can be taken from the peripheral circulation of the patient, or else from bone marrow through various techniques known in the sector.

Pre-Enrichment

The proportion of tumour cells in the sample taken can be enriched using various methods, such as for example: centrifugation on density gradient, constituted by solutions such as Ficoll or Percoll; mechanical enrichment, such as filters of various types; enrichment by means of separation by dielectrophoresis via a purposely provided device—dielectrophoretic-activated cell sorter (DACS); selective lysis, such as for example, selective lysis of erythrocytes not of interest; immunomagnetic separation, via immunomagnetic beads with positive selection (using beads bound to specific antibodies for the population to be recovered) or with negative selection (depletion of cell populations that are not of interest), and in which the two types of selection can be coupled in order to increase the specificity of the procedure; FACS, on cells labelled with a specific fluorescent antibody; solid-phase immunoseparation, advantageously by means of microfluidic systems presenting surfaces coated with specific antibodies for epithelial receptors (such as EpCAMs).

For the majority, these procedures can be automated and all the sorting procedures can be preceded by separation by centrifugation on density gradient or alternatively they can be applied on whole blood.

In general, the process starts with a dilution, but this is not strictly necessary for all techniques.

Other Enrichment Techniques

A further technique well known to persons skilled in the branch is the one referred to as MACS developed by Miltenyi Biotech, or else Easy-sep, developed by Stem-cell technologies.

Alternatively, it is possible to use paramegnetic beads of larger dimensions that do not require the use of a special column, but can also be used when working with wells or test tubes (such as, for example, anti-EpCAM Dynabeads).

To sum up, the step of enriching the specimen in the population of cells comprising at least one type of tumour cells can be performed via a method consisting of successive steps by means of a selection of cells made on the basis of at least one parameter chosen from the group consisting of:
a. mass density;
b. morphology;
c. electrical properties;
d. chemical properties;
e. mechanical properties;
f. expression of surface antigens;
g. expression of intracytosolic antigens;
h. dielectric properties;
i. magnetic properties;
j. geometrical properties (size, etc.); and
k. optical properties.
l. or combinations thereof.

Advantageously, the enrichment of the tumour cells is then further obtained by means of a second step, in which the positive or negative selection of cells is made from the mononucleated cells recovered in the first step. Obviously, the second enrichment step can comprise a selection made on the basis of the capacity to express or not a specific antigen, evaluated with one of the following techniques:
a. MACS, i.e., Magnetic-Activated Cell Sorter;
b. DACS, i.e., Dielectrophoretic-Activated Cell Sorter;
c. FACS, i.e., Fluorescence-Activated Cell Sorter.

Second Embodiment

Formalin-Fixed-paraffin Embedded Samples

Sampling

The samples are formalin-fixed and paraffin-embedded samples routinely used and prepared by known methodologies.

Sample Processing

The samples are deparaffinised and cells are dissociated with a 1% dispase/1% collagenase solution so as to obtain a cell suspension in a fluid which includes tumour cells and stromal cells. The methodology employed is known from Corver W E et al. (J Pathol, 206, 233-241 (2005).

Isolation of Single Tumour Cells (Common to Both Embodiments)

Next, the sample containing the tumour cells is inserted in a microfluidic device that is able to select individually single cells and isolate them in an automatic or semi-automatic non-manual way. For this purpose, it is possible to use a dielectrophoretic isolation (DEPArray, using for example, the techniques described in PCT/IB2007/000963 or in PCT/IB2007/000751, or again in Manaresi et al., IEEE J. Solid-State Circuits, 38, 2297-2305 (2003) and in Romani et al., Proceedings of the International Solid State Circuit Conference, 1, 224-225 (2004)), or else opto-electronic traps or optophoretic isolation or again, laser tweezers (see, for example, Reichle et al., Electrophoresis, 22, 272-82 (2002) or Fiedler et al., Anal. Chem., 70, 1909-15 (1998)).

The contents of said documents are incorporated herein as regards the relevant parts just for reference.

Identification of the cells of interest can be made, for example, via sensors:

external sensors;

optical sensors, such as a fluorescence microscope; or also internal sensors;

optical sensors, as disclosed in the patent Nos. WO2007049103 and WO2007010367, which describe an integrated method of identification of the fluorescent cells;

impedentiometric sensors, as disclosed in the patent Nos. WO2007049103 and WO2007010367, for the detection of impedentiometric characteristics of cells.

The signal for selection of the cells can be also indirect, such as, for example, the presence of a microbead coupled to an antibody, which is in turn coupled to the cell. The presence of one or more microbeads coupled to a cell can be detected as already described previously, by means of impedentiometric sensors or optical sensors (in clear field or in fluorescence).

According to the invention, by manipulating individually single tumour cells by means of a microfluidic device, preferably in an automated way, the tumour cells contained in the sample are isolated to constitute a purified specimen to be analysed having a purity of at least 90%.

Preferably, tumour cells are isolated to constitute a purified specimen to be analysed having a purity higher than 95%. Even more preferably, tumour cells are isolated to constitute a purified specimen to be analysed having a purity of 100%.

Genetic Analysis

On the tumour cells recovered according to the invention various types of analysis can be performed that enable genetic or chromosomal characterization thereof at different levels of resolution and sensitivity and according to the diagnostic purpose of the study, in accordance with what has been described previously.

For example, it is possible to proceed to sequencing of CTCs taken from patients presenting metastases in order to detect the presence of mutations of the K-RAS gene.

In the case of prostate cancer, it is possible to evaluate the presence of deletions on CTCs by means of single-cell whole-genome amplification.

Again, in the case of cancers of unknown primary origin (CUPs) it is possible to identify the original tissue via the genetic profile and/or the profile of expression of the CTCs, thus obtaining information that is fundamental for the choice of the most appropriate therapy.

In the case of disseminated tumour cells, then, it is possible to perform analysis of gene expression on single CTCs and/or DTCs in order to identify prognostic indicators and potential therapeutic targets.

In the case of FFPE derived cells, the ability to derive pure cellular subpopulations, including pure normal stromal cells and pure tumor cells, from individual FFPE samples and perform reliable and precise molecular analysis thereon enables meaningful retrospective correlative studies aimed at connecting cell genotypes to clinical histories.

PREFERRED EXAMPLES OF EMBODIMENTS OF THE INVENTION

By way of non-limiting example, a first preferred embodiment of the method according to the present invention is described hereinafter, following the flowchart represented in FIG. 1.

Starting Sample

In a sample of 17 ml of whole blood taken from a healthy male donor there were introduced by spiking 2000 cells belonging to the cell line of breast cancer MCF7.

Preliminary Enrichment

The preferential embodiment of the invention envisages a process consisting of successive steps.

(a) FICOLL. The sample, was treated with an anticoagulant (e.g., EDTA) and transferred, preferably within 8 h, into a 50-ml sterile test-tube made of polypropylene. From this a volume of 50 µl was extracted, which was used for counting white blood cells (WBCs) and red blood cells (RBCs) using a Coulter counter.

The sample was then diluted 1:4 with PBS and EDTA (2 mM) having a pH of 7.2.

A volume (≤30 ml) of diluted blood was accurately stratified on 15 ml of Ficoll-Hypaque (density=1.077 g/ml).

Next, the sample was centrifuged at 654 g for 30 min at 22° C. in a (brakeless) tilt-rotor centrifuge.

The plasma was removed with a pipette (of the Pasteur type)—but an automatic pipettator may also be used—taking care not to interfere with the layer of lymphocytes at the interface. The layer was carefully collected with a drop-counter and transferred into a 50-ml polypropylene sterile conical test-tube.

The test-tube was filled with PBS and EDTA (2 mM), shaken and centrifuged at 300 g for 10 min at 10° C.

The supernatant portion was rejected.

The test-tube was filled with PBS and EDTA (2 mM), and again shaken and centrifuged at 300 g for 10 min at 10° C. The supernatant portion was drawn off.

From the sample the cell pellet (i.e., the complex of the peripheral-bloodflow mononucleated cells, PBMNC) was taken, to be re-suspended in 5 ml of buffer. From this was taken an aliquot of 50 µl to carry out the WBC count with a Coulter.

The test-tube was filled with buffer, shaken and centrifuged at 200 g for 10 min at 10° C. The supernatant portion was rejected.

An alternative to Ficoll as first step of pre-enrichment for eliminating the erythrocytes is represented by selective lysis of erythrocytes, which exploits chemical properties of the cells.

(B) CD45 MACS Depletion

The cell pellet was re-suspended in 80 µl of buffer for a total of $10^7$ cells.

An amount of 20 µl of microbeads of anti-CD45 were added for a total of $10^7$ cells. There followed steps of shaking and incubation for 15 min at 4° C.

The cells were washed by filling the test-tube with buffer and centrifuging at 300 g for 10 min at 10° C.

The supernatant portion was rejected and the cell pellet was re-suspended in 500 µl of buffer for a total of $10^8$ cells.

The MACS column of LS type (Miltenyi) was positioned within the magnetic field of a suitable MACS separator, according to the indications provided by the manufacturer.

A pre-filter was positioned on each column.

Both the pre-filter and the column were prepared by rinsing with 3 ml of buffer.

The cell suspension was applied to the column (or on the pre-filter).

The test-tube that contained the cell suspension, now empty, was filled with 9 ml of buffer.

The non-labelled cells were collected, and the column was washed by adding for three times 3 ml of buffer, taking it each time from the test-tube filled in the previous step.

The column was removed from the separator and set on a test-tube.

An amount of 5 ml of buffer were introduced into the column using a pipette.

The fraction containing the magnetically labelled cells was expelled immediately afterwards by operating the plunger.

To reduce the number of contaminating cells further, it is possible to use a depletion cocktail with further magnetic microbeads functionalized with antibodies that recognize antigens present selectively on cells to be depleted, such as for example, anti-GPA microbeads (to eliminate the residual erythrocytes from the Ficoll).

To reduce the number of contaminating cells even further, it is possible to carry out a second passage in a magnetic column.

(C) Fixing and Labelling

The post-MACS cells were centrifuged at 300 g for 10 min; the pellet was re-suspended in 40 µl of buffer.

The specimen was transferred into a 1.5-ml test-tube. To this were added 760 µl of 4% paraformaldehyde just prepared, followed by incubation for 20 min at room temperature.

After centrifugation at 0.2 r.c.f. r.p.m. for 5 min in the microcentrifuge, the supernatant fraction was drawn off.

This was followed by washing with 1 ml of PBS, centrifugation at 0.2 r.c.f. r.p.m. for 5 min in the microcentrifuge, and the supernatant fraction was again aspirated.

To this were added 100 µl of PBS/BSA at 3% (blocking buffer).

The specimen was incubated for 10 min at room temperature.

After further centrifugation at 0.2 r.c.f. r.p.m. for 5 min in the microcentrifuge, followed by aspiration of the supernatant fraction, staining was performed with EpCAM-FITC and CD45-PE (Miltenyi, according to the protocol recommended by the manufacturer).

To complete the process, a final washing was performed with 1000 µl of Super Buffer (Hepes 400 mM, 1% BSA) and 1 µl of Hoechst 33324 diluted with water (100 µg/ml) and the specimen was vortexed.

The specimen was subjected to a quality control to verify the intensity of fluorescence of the marker and the total cell concentration. A part of the labelled specimen was re-suspended in a minimum volume of specific buffer, useful for dielectrophoretic manipulation, and was loaded on a device for control of quality of the specimen and controlled under the fluorescence microscope: the intensity of fluorescence of the cells was noted in the different channels and a count was made of the cells labelled in Hoechst 33324 (total nucleated cells). If the cell concentration was higher than the optimal one for proper operation of the device for isolation of the single cells, the next step was dilution of the specimen to obtain the desired concentration.

Isolation

Figure 2:
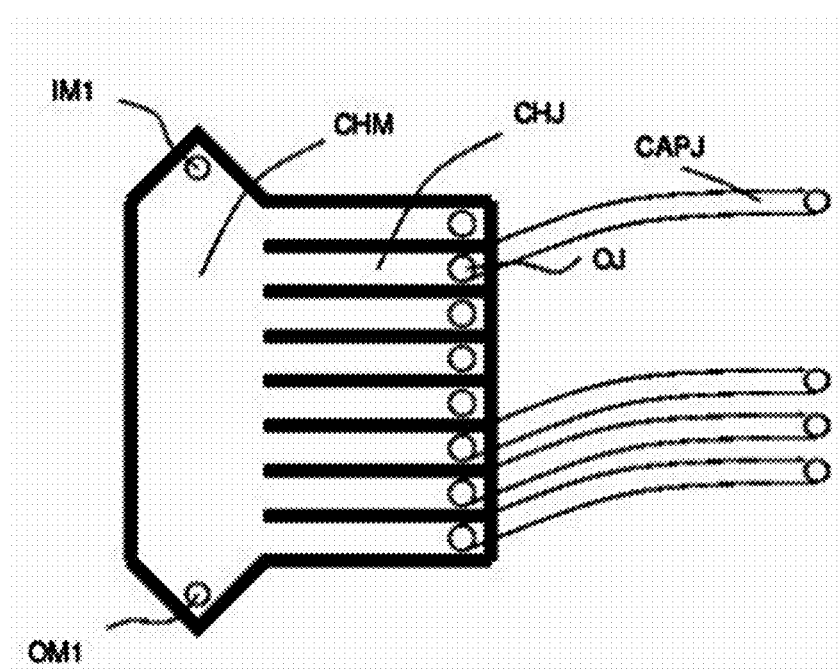
FIG. 2 is a schematic illustration of an example of device for implementing the method (or the substantial and characterizing part thereof) according to the invention.

The cells thus obtained were then inserted in the chip DEPArray® CONV600K (manufactured by Silicon BioSystems, see for example, the document No. WO0069525) for dielectrophoretic manipulation and isolation of the tumour cells. The device as a whole is illustrated in FIG. 2.

The sample was subjected to scanning, identification, and selection, sorting, and recovery of the tumour cells.

The caged cells were scanned in an automatic or manual way at the microscope with 3 different fluorescence channels (i.e., in 3 different wavelengths). Observation in the DAPI channel (where by "DAPI channel" is meant UV excitation and emission in the blue, which is hence used also for visualization of Hoechst 33324) enables identification of the (positive) nucleated cells, whilst observation in the channels for EpCAM and CD45 enables differentiation between tumour cells (DAPI+, EpCAM+ and CD45−, with compatible morphology), lymphocytes (DAPI+, EpCAM−, CD45+) and spurious signals (DAPI+, EpCAM+ and CD45+ or also DAPI−, EpCAM+ and CD45+, or DAPI+, EpCAM+ and CD45− with morphology incompatible with tumour cells).

FIGS. 3A-B-C show images acquired in the course of scanning of the cells of the specimen within the DEPArray® CONV600K. More in particular, FIG. 3A shows the images for three tumour cells in the three channels taken into consideration. FIG. 3B shows the images for a spurious cell in the three channels taken into consideration. FIG. 3C shows the images for two lymphocytes in the three channels taken into consideration.

Selection of cells was then performed by selecting the cages containing the cells found positive to DAPI (nucleated cells), positive to EpCAM and negative to CD45. Sixteen cells were identified on the chip, some of which were double. Fifteen cells, some of which were double, were finally recovered in a few microlitres (<40 µl) in a 0.2-ml PCR tube.

The final analysis was performed using an Applied Biosystems Minifiler Kit.

Figure 4A:
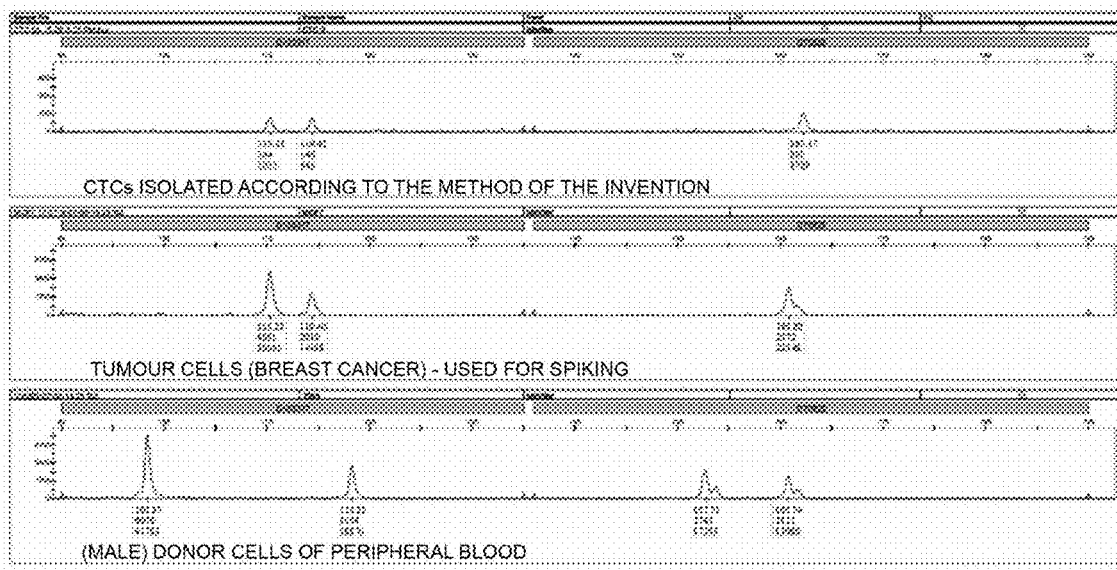
FIGS. 4A, 4B, 4C and 4D show a series of electropherograms obtained in the course of the genetic analysis of circulating tumour cells identified and isolated according to the method of the invention.
Figure 4B:
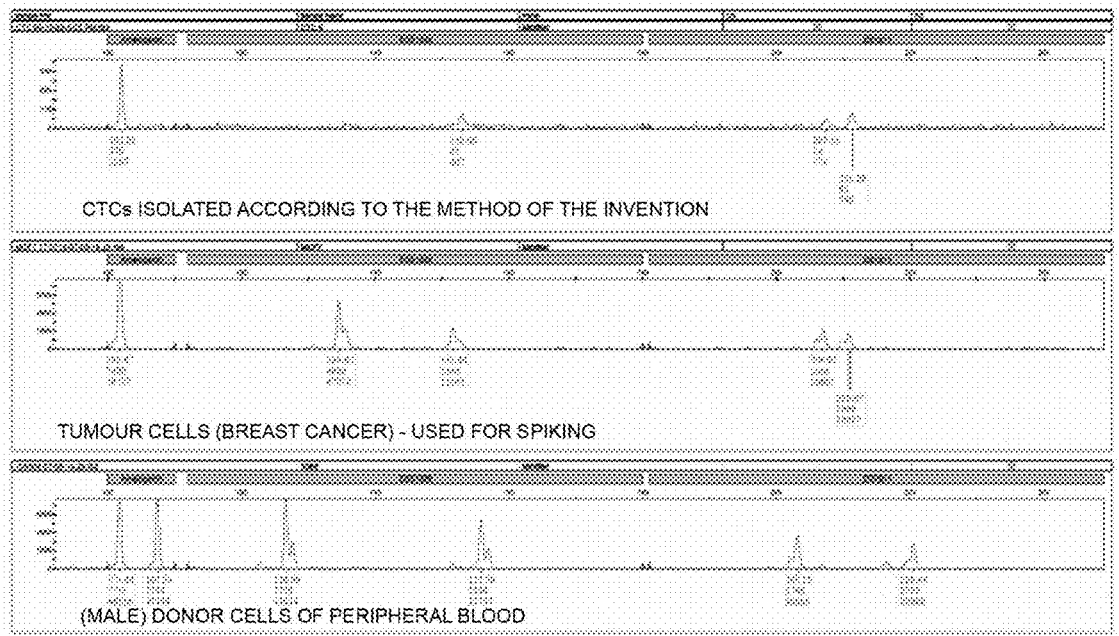
Figure 4C:
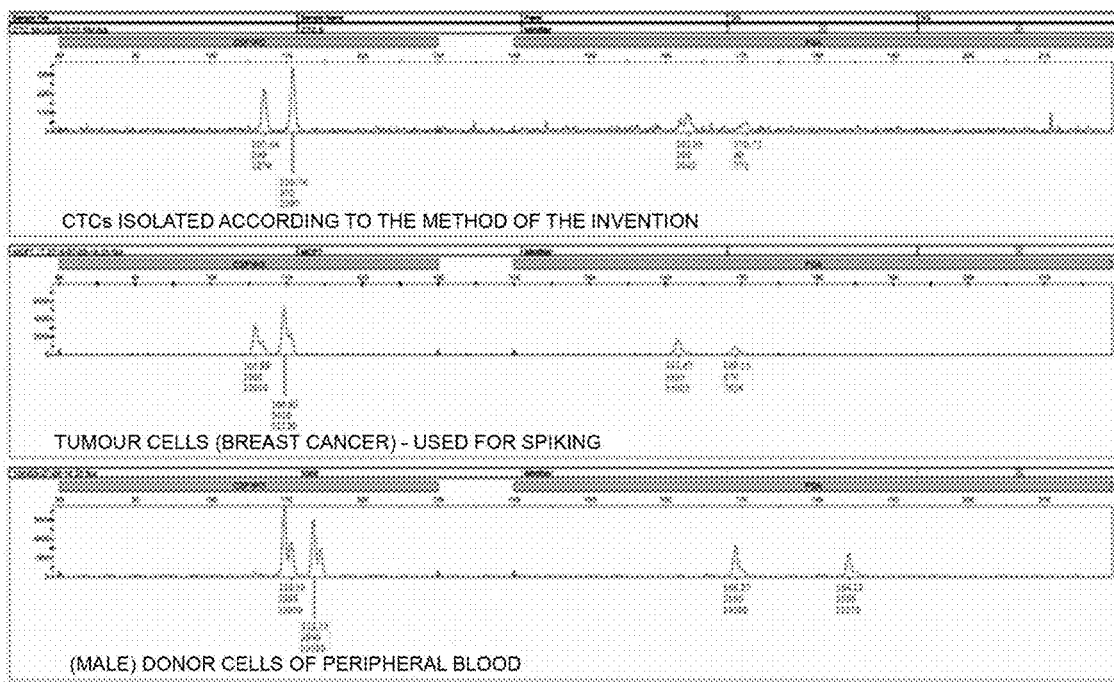
Figure 4D:
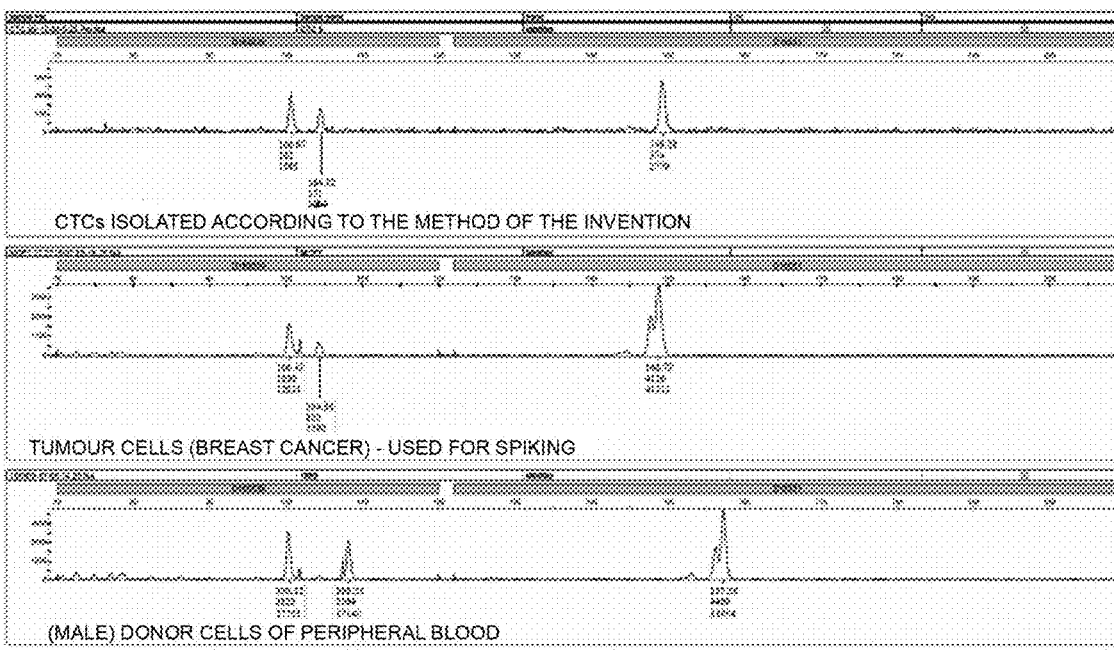

Given in FIGS. 4A-B-C-D are the results of the analysis of the fragments (QF-PCR) performed using a Minifiler Kit. In the four fluorescence channels taken into consideration, different microsatellites were analysed. It may be noted how in no case were there traces of contamination by alleles coming from the male subject into whose blood the tumour cells were introduced by spiking.

As an alternative to the anti-EpCAM antibody, it is possible to use a different type of antibody, such as, for example, an antibody that recognizes one or more types of cytokeratin, which is not expressed in the blood cells.

Alternatively, it is possible to use an antibody that is more characterizing for cancer (tumour-specific), such as for example:

for the prostate, the Prostate Specific Antigen (PSA);
for the lung, the Thyroid Transcription Factor 1 (TTF-1);
for the breast, the Human Epidermal growth factor Receptor 2 (HER2/neu)

Possibilities of Application

Obtaining a specimen of CTC having a purity of 100%, following upon an automatable procedure of selection and isolation, renders feasible diagnostic pathways for a plurality of conditions that, otherwise, could not be analysed accurately, reliably, and precisely.

Example 1

Non-invasive evaluation of mutations (for example, in the K-RAS gene) in cancer patients.

Described in what follows is the case of isolation of CTCs from peripheral bloodflow of patients affected by metastatic Colon-Rectal Cancer (mCRC).

Figure 5:
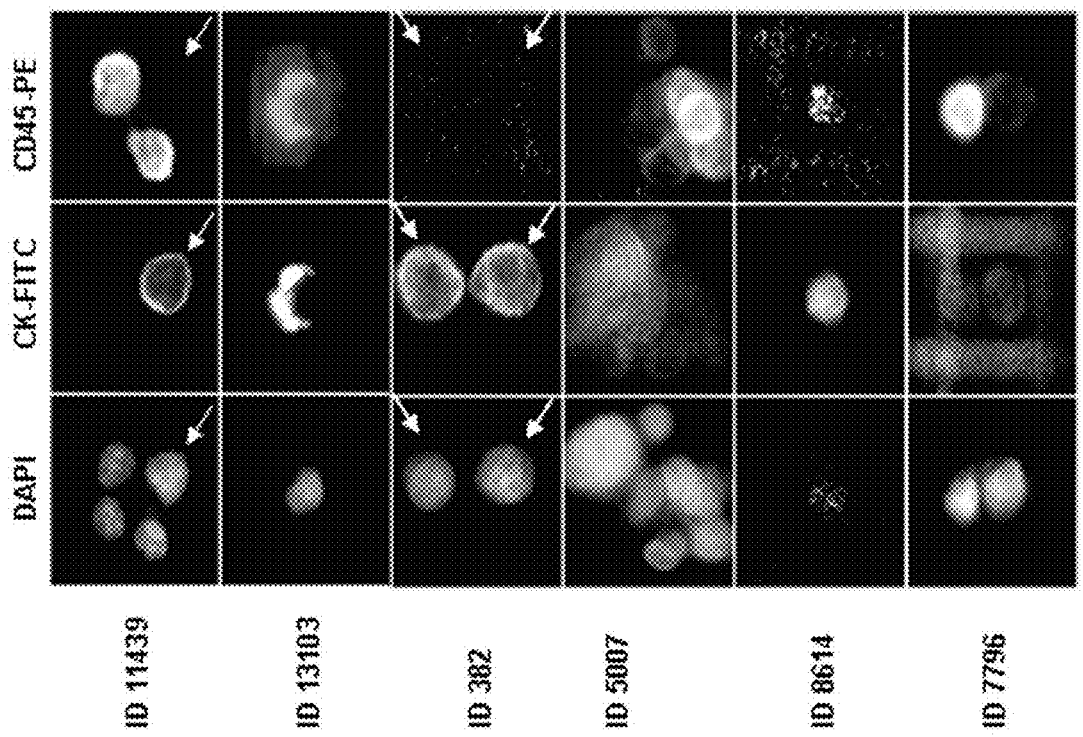
FIG. 5 shows images acquired in the course of scanning of circulating tumour cells selected and isolated according to the method of the invention from peripheral bloodflow of patients affected by mCRC.

A specimen of 7.5 ml of peripheral bloodflow was drawn from the patient in Vacutainer tubes with EDTA anticoagulant (Beckton Dickinson). The specimen was analysed with Coulter Counter (Beckman Coulter) and presented $42 \times 10^6$ leukocytes (WBCs) and $43.95 \times 10^9$ erythrocytes (RBCs). The PBMCs were then isolated via centrifugation (in Ficoll 1077). The PBMCs recovered ($16.5 \times 10^6$ on the basis of the count with Coulter Counter) were washed in PBS with BSA and EDTA (Running Buffer, Miltenyi) and were selected via depletion with magnetic microbeads conjugated to anti-CD45 and anti-GPA antibodies (Miltenyi) according to the instructions of the manufacturer. The resulting cells (negative fraction for CD45 and GPA) were fixated with 2% PFA in PBS for 20 min at room temperature (RT). This was followed by washing in PBS and incubation in 3% PBS/BSA (blocking buffer), for 10 min at room temperature. After a flushing in PBS, CD45 labelling was performed with 10 µl of PE-conjugated anti-CD45 antibody (Miltenyi) in 100 µl of Miltenyi Running Buffer (RB) for 10 min at 4° C. The reaction was blocked by adding 1 ml of RB, centrifuging, and drawing off the supernatant portion. The cells were then permeabilized with 90 µl InsidePerm (Miltenyi) and simultaneously labelled with 10 µl of FITC-conjugated anti-CK antibody for 10 min at room temperature. The reaction was terminated by adding 1 ml of Inside Perm, centrifuging, and removing the supernatant fraction. The pellet was re-suspended in buffer optimized for manipulation of cells fixated and permeabilized with dielectrophoresis—Hepes (400 mM)+BSA (2%) in water (SB)—and DAPI (1 mg/ml) and, finally, washed in SB and re-suspended for injection into the chip DEPArray™ CONV600K (with 100,000 dielectrophoretic cages). Present on the chip were approximately 16,000 cells. After scanning in DAPI/FITC/PE the CTCs were identified. FIG. 5 contains images of CTCs (indicated by a white arrow) selected and isolated by means of the method of the invention, said images being appropriately processed so as to highlight the fluorescence in three respective channels: FITC-conjugated anti-CK MoAb (Miltenyi) in the green channel; PE-conjugated anti-CD45 MoAb (Miltenyi) in the red channel; and DAPI labelling of DNA for identification of the nuclei in the blue channel.

It should be noted how it is possible to distinguish clearly between various types of possible events from an analysis of the processed images, whereas in a less refined analysis that is not based upon images, but only upon the intensity of the overall fluorescence, the images could be rejected as false positives.

For example, the cage with ID 382 contains a pair of CTCs. These were evidently already bound at the start, since the probability of two of the three CTCs present ending up in one and the same cage is negligible. Without image analysis, this event could have been rejected since, in general, clusters of cells can give rise to spurious fluorescence signals given that the antibody—for example, anti-CK—gets trapped in a non-specific way. Recovery of the two ID382 cells hence has a purity of 100% (and is compatible with the majority of molecular analyses).

The cage with ID 11439 indicates a DAPI+/CK+/CD45+ event. Without image analysis said event could have been rejected as spurious, but, instead, since the image makes possible detection of the distribution of fluorescence in the event, it is possible to interpret the datum as referring to a DAPI+/CK+/CD45− CTC (indicated by a white arrow) caged together with three other CK− nucleated cells, two of which CD45+. The contents of said cage can be recovered separately. Using a system based upon mobile dielectrophoretic cages, the segregation in single cages of the cells that initially share the same cage can be performed by applying appropriate patterns of cages. If it is not possible to segregate the CTC from the other contaminating cells of the cage, it is possible in any case to recover the contents of the cage, associating to said recovery the information of the presence of contaminants. This is a further advantage of the technique according to the invention. The purity of the cells recovered is noted down and this can be taken into account in the analysis downstream. In the case in point, the cell could hence be recovered together with the other three (a purity of 25%), or else separated and recovered alone to obtain a pure recovery of 100% (if isolated alone), or else of 50% if isolated together with a contaminant, or of 90% if isolated together with a contaminant and a further nine CTCs, without contaminants possibly present in other cages (not in this case).

The cage ID 5007 shows an event which, on the basis of the total fluorescence, would appear similar to that of ID 11439 since it is a DAPI+/CK+/CD45+ event. However, on the basis of the image, it is possible to determine how it is a spurious event in so far as it is linked to a cluster that has trapped anti-CK antibodies.

The cage ID 13103 shows an event that, on the basis of the total fluorescence, would appear similar to that of ID 11439 since it is a DAPI+/CK+/CD45+ event. However, on the basis of the image, it is possible to determine how as it is a spurious event in so far as it is linked to a single positive double cell with CD45+(non-CTC) signal.

The cages with ID 8614 shows an event CK+/CD45− but DAPI−, not classified as CTC. The cage with ID 7796 shows a control event (two white blood cells) comprising two cells that are not classified as CTCs, because they are CK− and one is also CD45+.

The cells of interest can hence be isolated or otherwise, according to the purposes of the experiment, in terms of purity of the specimen and according to the ease of separation of the cell from an agglomerate of cells within which it is comprised. In this sense, the selection based upon images is particularly effective for exclusion of false positives and false negatives.

As an alternative to Ficoll, it is possible to use a technique based upon selective lysis of red blood cells (RBCs). In this case, in the specimen there remain in the first instance also the granulocytes. After said removal of the RBCs, the tumour cells can be further enriched via positive immuno-magnetic selection (e.g., with magnetic microbeads coupled to anti-EpCAM antibodies), or negative immuno-magnetic selection (e.g., via magnetic microbeads coupled to anti-CD45 antibodies or to a cocktail with anti-CD45 and other antibodies against antigens not present in the CTCs). In any case, the few CTCs present are obtained in a specimen containing tens of thousands or hundreds of thousands of leukocytes.

Isolation of the CTCs from the peripheral bloodflow is likewise compatible with procedures of enrichment and labelling approved by the FDA, such as the Veridex Cell-Search™ system. In this case, the CellSearch system can be used also for carrying out labelling and enrichment in an automated way (with the AutoPrep machine). With this system, the few CTCs present are obtained (with an optimal yield of around 90%) in a specimen with typically only a few thousands of contaminating leukocytes (typical values of 1000-5000). The CellSearch AutoPrep represents an excellent enrichment system, and has as its main limitation the fact that it is based upon an EpCAM-positive immuno-magnetic selection. Consequently, in some types of tumours, where the CTCs do not over-express EpCAM, it would be possible to find only a few CTCs. In such cases, the negative selection is more indicated for depletion of CD45+ cells.

Detection of the mutational status of the K-RAS gene has considerable clinical importance, since it has been demonstrated that some mutations of K-RAS are connected to the inefficacy of therapies based upon monoclinal antibodies directed against the EGFr receptor. Said mutations, in fact, activate, downstream, the mechanism of cell proliferation in spite of the EGFr inhibition upstream. Therapies with Cetuximab and Panitumumab are already indicated only for patients with wild-type K-RAS. The possibility of identifying the mutation in CTCs affords the possibility of not having to resort to a biopsy, in particular in all those circumstances in which a biopsy is not possible or is very complex to perform. Even when tissues removed surgically are available, the possibility of analysing CTCs is in any case interesting. The tumours are intrinsically unstable from the genetic standpoint, and the metastases can derive from cells located in sites distinct from that of the primary tumour; consequently, the CTCs can reflect better the molecular profile of the cells undergoing metastasis.

In order to verify the possibility of detecting mutations of K-RAS from CTCs, CTCs from peripheral bloodflow of patients affected by metastatic cancer of the colon-rectum (mCRC) were analysed. Following the enrichment procedure described above, CTCs were identified and isolated on the DEPArray™. The purity of 100% enables detection of the possible presence of the mutation via sequencing: after prior amplification of the starting copies, for example with nested PCR, sequencing is carried out using known techniques.

In the case in point, the analysis downstream was performed using the DOP-PCR technique with the Omniplex kit produced by Sigma. After amplification, the product was analysed with a capillary-electrophoresis sequencer manufactured by Applied Biosystems.

Figure 6:
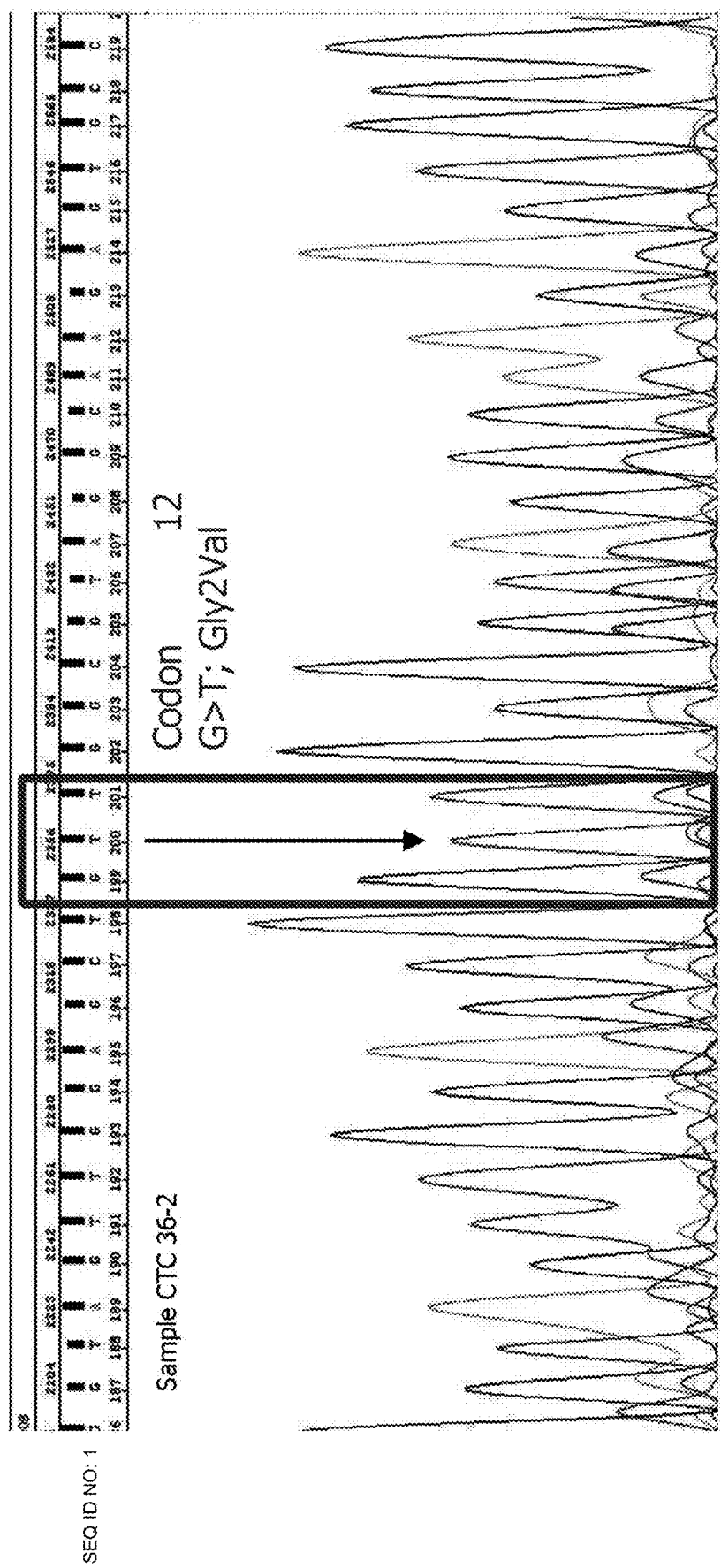
FIGS. 6 and 7 show, respectively, spectra regarding the detection of a mutation Gly2Val on K-RAS (respectively SEQ ID NO:1 and 2) of CTCs isolated from the peripheral bloodflow of a patient affected by mCRC according to the method of the invention.
Figure 7:
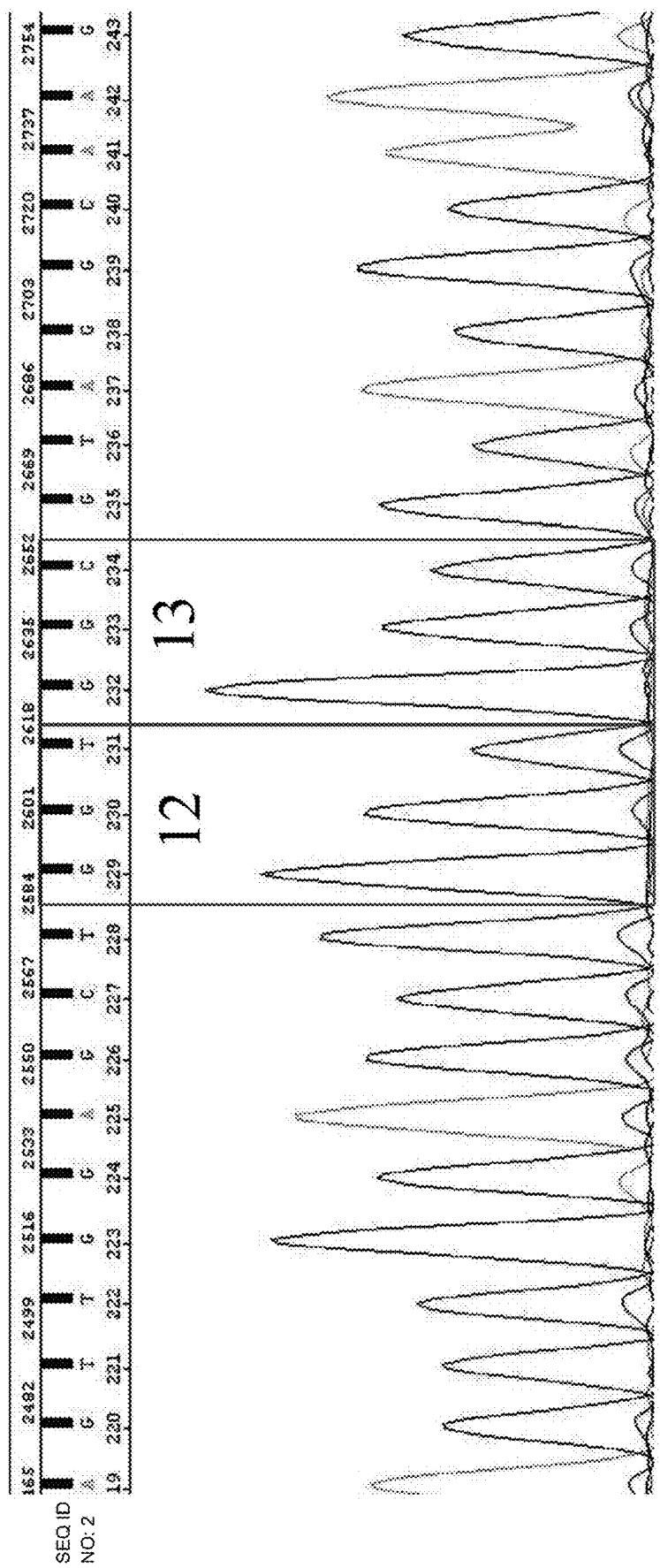

FIG. 6 shows an example (SEQ ID NO:1) of detection of a mutation in one of the specimens analysed, which corresponds to a mutation from glycine to valine in the codon 12 (shown in FIG. 7 is the corresponding negative control (SEQ ID NO:2)).

Example 2

Evaluation on CTCs of deletions (for example, in prostate cancer) via single-cell whole-genome amplification and CGH array. In this case, there is advantageously performed isolation of the single cells to be recovered in different wells. In this way, the analysis takes into account the heterogeneity of the population, and supplies not only the average, but multiple signals regarding each cell so that it is easier to identify mutations present only in some of the tumour cells.

Example 3

Non-invasive identification of the original tissue in CUP tumours, via genetic profile and/or profile of expression of the CTCs.

Example 4

Analysis of gene expression on single disseminated tumour cells (DTCs) for identification of prognostic indicators, and potential therapeutic targets. Also in this case, there is advantageously performed isolation of the single cells to be recovered in different wells. In this way, the analysis takes into account the heterogeneity of the population, and supplies not only the average, but multiple signals for each cell so that it is easier to identify mutations present only in some of the tumour cells.

Example 5

As already mentioned, in general, what has been said above regarding "isolation of cells" is to be understood as applying also to "isolation of portions of cell", such as, for example, the nucleus. In fact, this enables in any case, for certain types of biomolecular information, significant information to be obtained (for example, by evaluating the genomic DNA contained in the nucleus).

In the example of isolation of a nucleus, the selection of the cells can be performed via techniques that mark in a distinguishable way the nuclei of tumour cells (CTCs or DTCs) from non-tumour cells, such as for example, FISH. In this case, the presence of multiple signals reveals the presence of duplications of genomic DNA (a characteristic of the tumour cells in general not present in normal cells).

In particular, in the example of breast cancer, it is of interest to evaluate duplication of the genomic region regarding the HER2 gene, normally located on chromosome 17. Hence, two types of probes are applied, one for the centromere of chromosome 17, and one for the HER2 gene. If the gene/chromosome ratio is higher than two the cell is conventionally considered positive to the test. Said information has, for example, implications in the use of drugs such as Trastuzumab (Herceptin) that present efficacy only in the case of over-expression of the corresponding HER2 receptor. Not only counting, but also identifying and isolating said cells in a purified form enables acquisition of further information on the genetic characteristics of the tumour.

Example 6

The presence of copy-number variations (CNVs) in the DNA constitutes a typical characteristic of a tumour. For evaluation of new drugs it is of considerable interest to be able to evaluate the CNVs in order to associate them to the course of the illness and, potentially, to areas of the genome in which the CNVs have a significant influence on the course of the illness (both in the case of favourable prognosis and in the case of unfavourable prognosis). This information can be helpful in identifying genes that could be targets for the pharmacological action. Furthermore, in the stage of diagnosis of cancer it may then be possible to identify in a minimally invasive way the CNV profile of the CTCs of the patient in order to orient the therapy on the basis of the experience acquired.

To demonstrate the possibility of determining CNVs small specimens of CTCs and, accordingly, small negative-control specimens were separated and isolated.

From a patient suffering from metastatic breast cancer (mBrCa), a specimen of 7.5 ml of peripheral blood was taken and put in a CellSave tube (Veridex). The specimen was enriched and labelled with fluorescent antibodies (PE-conjugated anti-CK, APC-conjugated anti-CD45) and DAPI, with the CellSearch AutoPrep, according to the standard procedure. The enriched cells were extracted from the Veridex cartridge, and re-suspended in a reduced volume. Said specimen was injected on the chip DEPArray™ A300K (Silicon Biosystems S.p.A.)—with 307,200 electrodes and a number of programmable cages, typically between 19,200 and 76,800. After scanning, there were isolated two negative controls with five cells, two specimens with five CTCs, one specimen with a single CTC.

Figure 8:
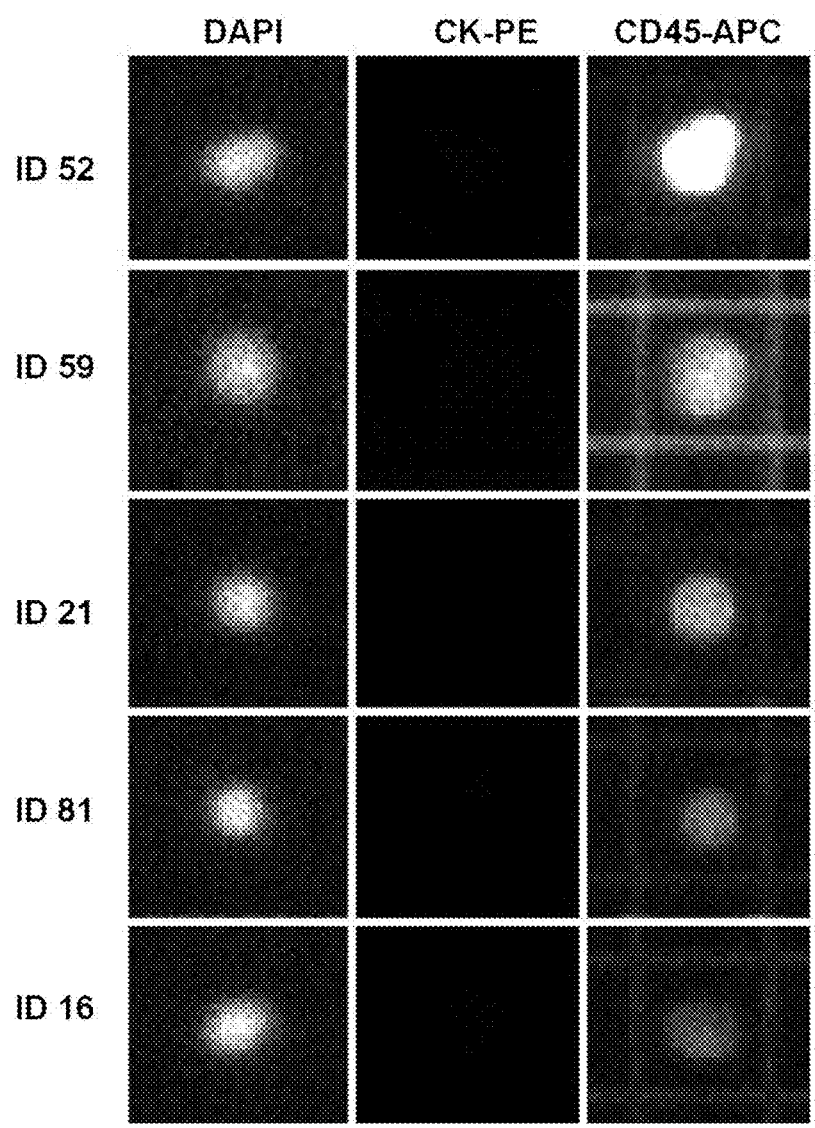
FIGS. 8, 9 and 10 each show five images acquired in the course of scanning of an enriched specimen, said images regarding the contents of five dielectrophoretic cages on a DEPArray™ chip. The cells of each figure were recovered together with one another and separately from the cells of the other figures.
Figure 9:
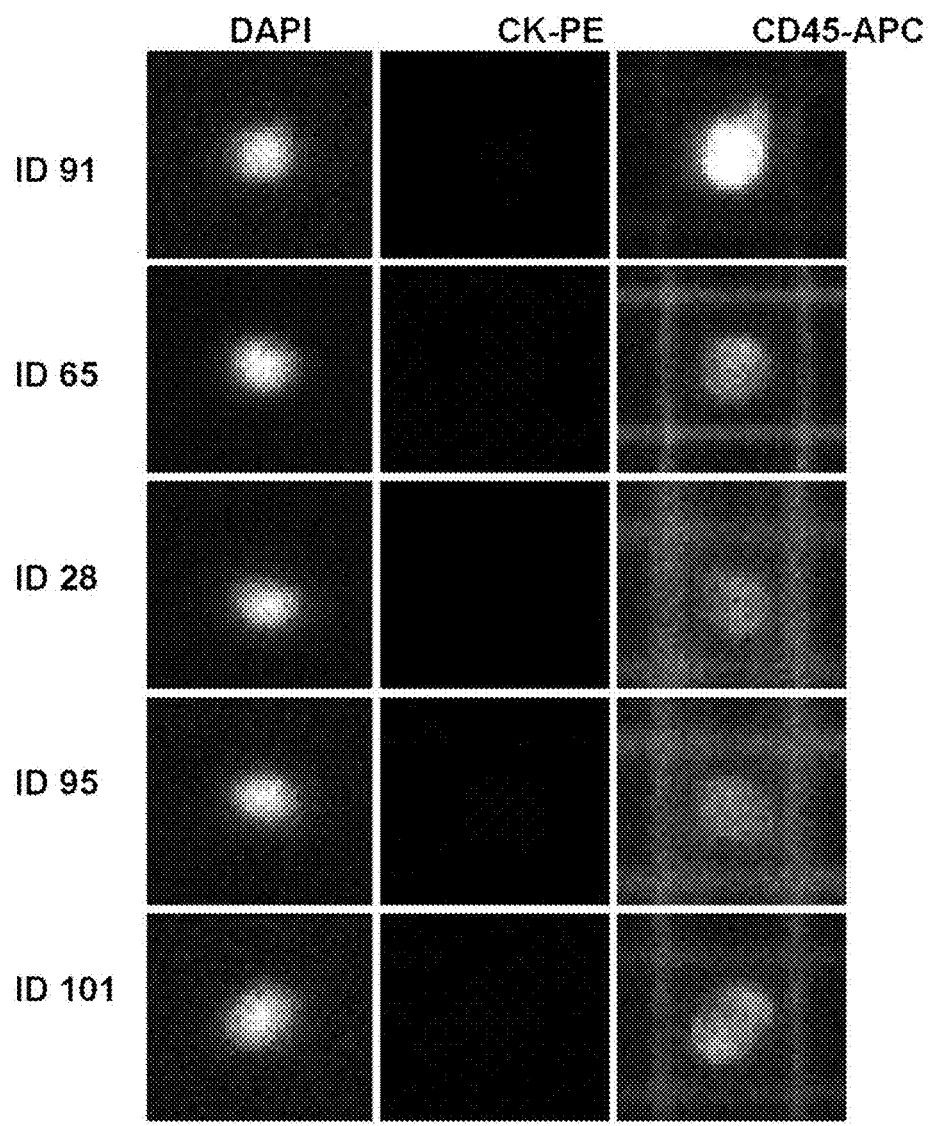
Figure 10:
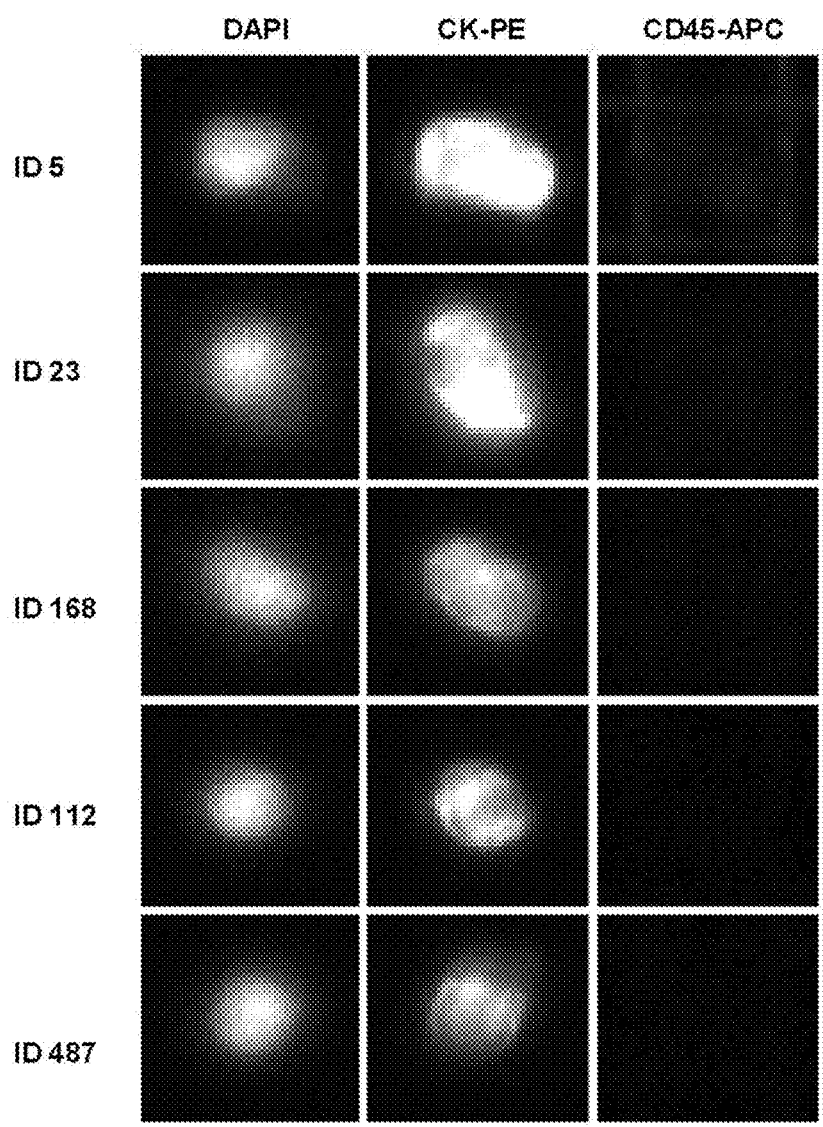

FIGS. 8 and 9 illustrate the cells recovered, respectively, in a first and second recovery with five leukocytes each (DAPI+/CD45+/CK−) as negative control for the CNV detection. FIG. 10 illustrates the five CTCs recovered separately, which form the subject of CNV analysis.

After selection and isolation performed using the method according to the invention, and given that a specimen is now available with a degree of purity higher than 90% (in the case in point, 100% for the recovery of CTCs illustrated in FIG. 10), it is possible to carry out successfully analysis based upon whole-genome amplification, according to a methodology illustrated in the document No. EP1109938, ligation-mediated PCR, followed by metaphase comparative genomic hybridization (CGH) or CGH array, which, with specimens of lower purity, would be impossible or intrinsically unreliable in so far as the signal detected would be too weak or fuzzy in the presence of non-tumoural cells.

A second preferred embodiment of the method according to the present invention is described hereinafter.

Starting Sample

The possibility of identifying and isolating single and pure tumour and stromal cells from FFPE archived tumour patient samples (e.g. cervical carcinoma or lung cancer) with DEPArray® technology for DNA analysis was investigated.

Sample Treatment

The sample re-suspension and keratin, vimentin, DAPI cell staining procedure for FFPE samples was performed according to the protocol published in Corver W E et al. (J Pathol, 206, 233-241 (2005).

Isolation

A small amount of the labelled cell suspension thus obtained (and estimated to be a few thousand cells) was loaded into the DEPArray™ cartridge (manufactured by Silicon BioSystems, see for example, the document No. WO0069525) for analysis.

The caged cells were scanned at the microscope with 3 different fluorescence channels (i.e., in 3 different wavelengths). Observation in the DAPI channel enables identification of the (positive) nucleated cells as well as quantitation of DNA content, whilst observation in the channels for vimentin and keratin enables differentiation respectively between stromal cells (DAPI+, vimentin+, keratin−), tumour cells (DAPI+, vimentin−, keratin+), and spurious signals (other combinations).

Figure 11A:
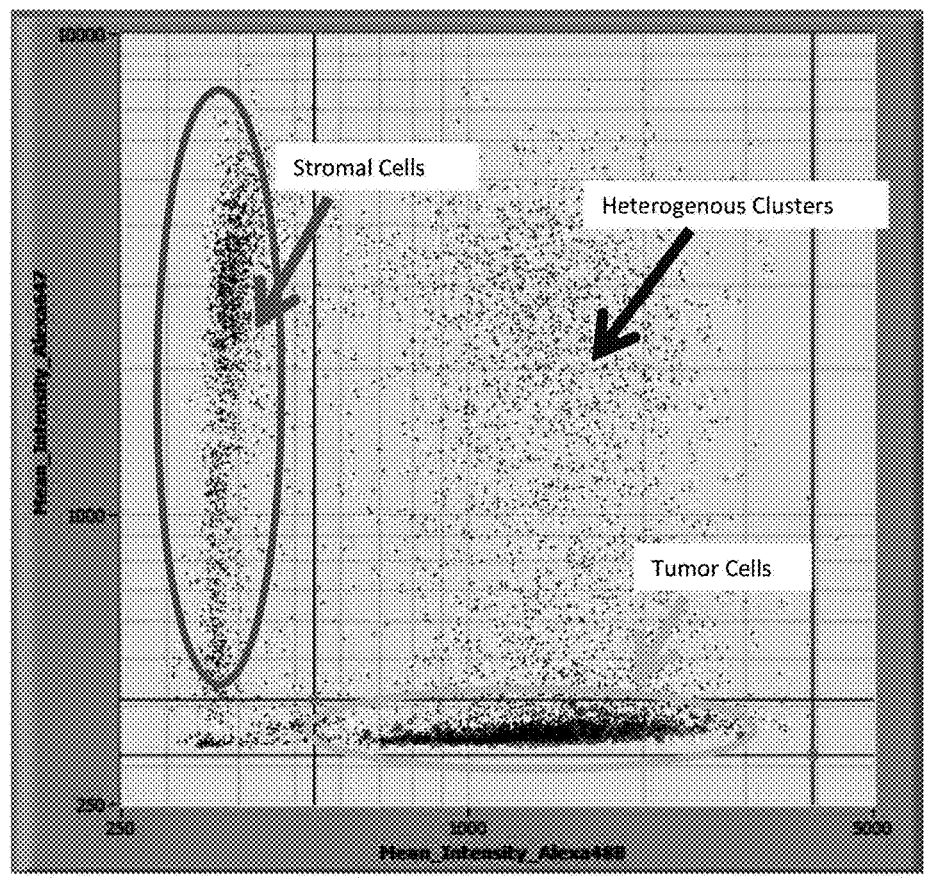
FIG. 11A shows a vimentin/keratin scatter plot generated by the DEPArray™ instrument for a FFPE derived sample.

FIG. 11A shows a scatter-plot generated by the DEPArray® instrument, in which two well defined populations of cells are clearly distinguishable: stromal cells (vimentin+/keratin−) on the upper left side and tumour cells (vimentin−/keratin+) on the bottom-right side.

Figure 11B:
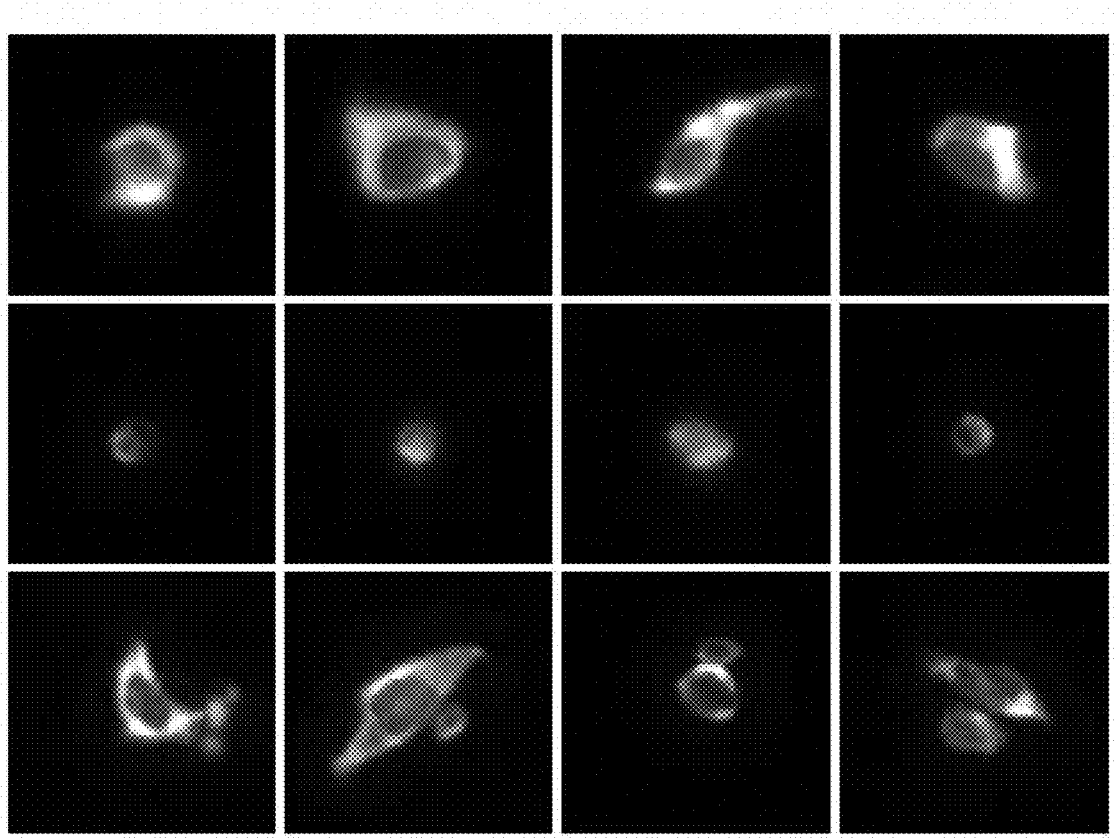
FIG. 11B shows DEPArray™ image galleries of tumour cells marked with keratin (top row), stromal cells marked with vimentin (middle row) and clusters of both populations (bottom row) derived from a FFPE sample.

FIG. 11B shows DEPArray™ image galleries of tumour cells marked with keratin (top row), stromal cells marked with vimentin (middle row) and clusers of both populations (bottom row). The image based sorting allows to clearly distinguish between single cells and heterogeneous clusters.

Figure 11C:
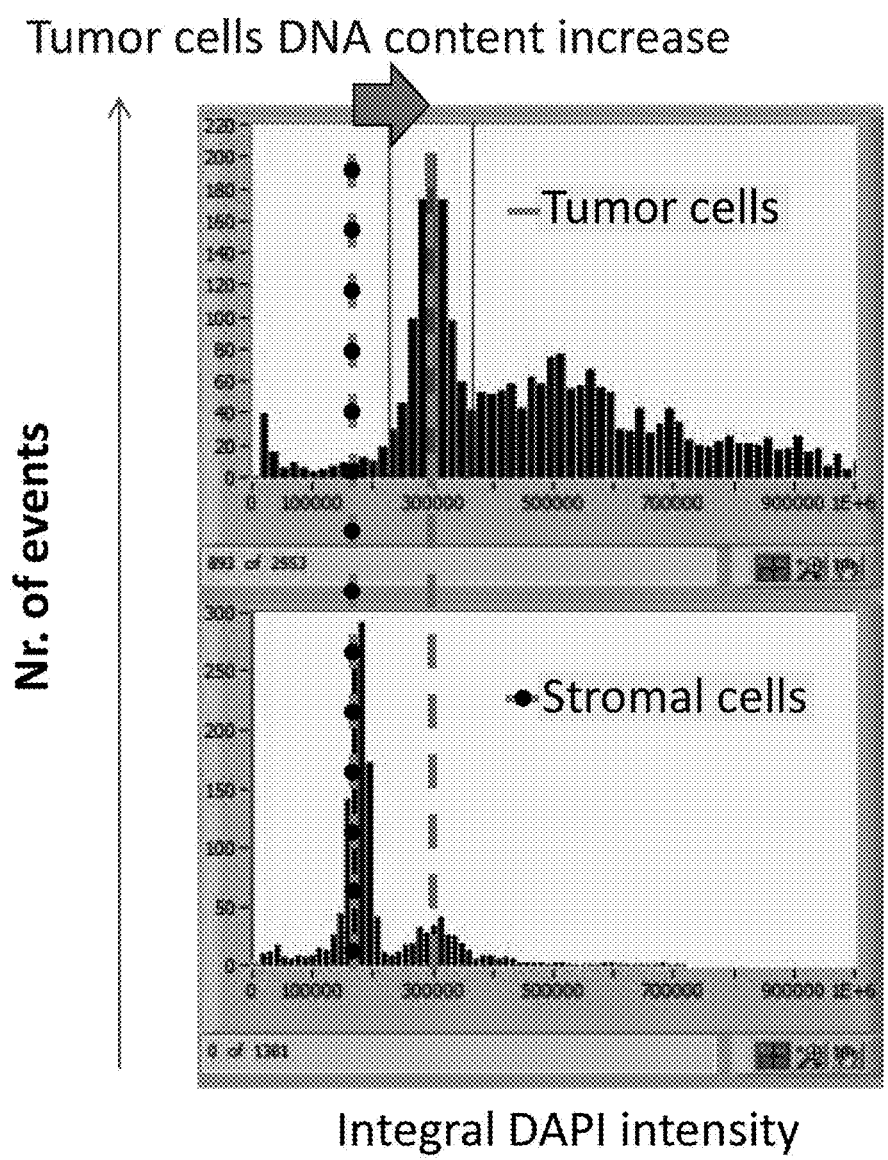

FIG. 11C shows the analysis of DAPI content of tumour and stromal cells obtained with the DEPArray™. The analysis of tumour cell ploidy was carried out by comparison with stromal cells using the measurement of integral DAPI fluorescence intensity linked to total DNA content. As expected for certain hyperdiploid tumors, the results show DNA gains in the tumour compartment versus the stromal compartment.

Pure recoveries of tumour and stromal cells were successfully carried out.

The above results show that it is possible to work with a very small amount of cells (about 3-4 orders of magnitude less than is necessary when using FACS). Moreover, the possibility of visualising the events detected as in FIG. 11b allows to select only the best and most pure cells for sorting. The purity obtained allows to carry out a more accurate downstream analysis, improving the sensitivity of the detection of presence/absence of different biomarkers. The possibility of selectively isolating only cells of interest further allows to perform a more in-depth genomic analysis as the background of unwanted cells is eliminated, thus for example revealing rare mutations among tumour cell populations.

Figure 12A:
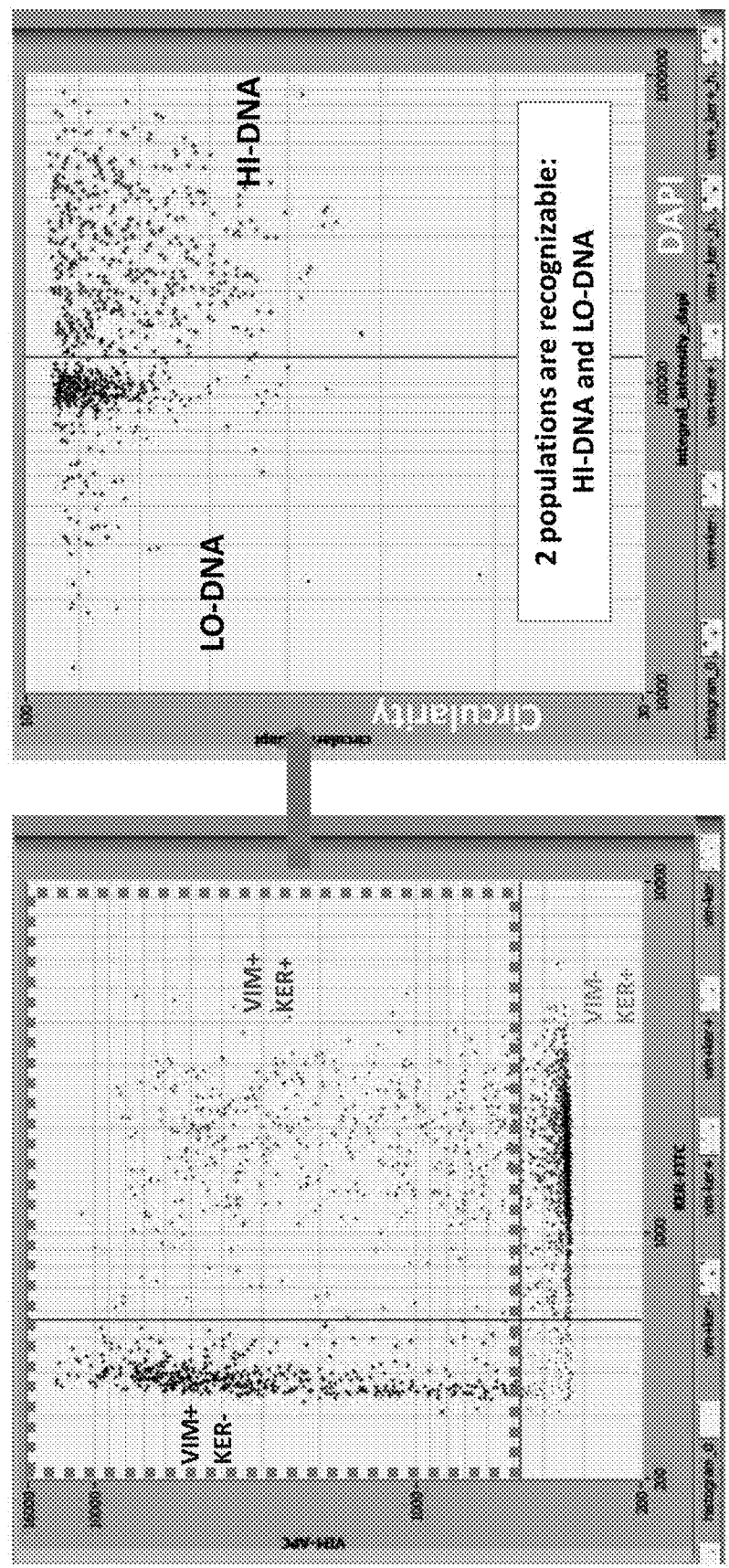
FIG. 12A shows a vimentin/keratin scatter-plot on the left and a scatter plot for integral DAPI intensity on the right generated by the DEPArray™ instrument for a FFPE derived sample.

FIG. 12A shows a vimentin/keratin scatter-plot on the left and the integral intensity DAPI scatter on the right. The integral intensity DAPI parameter allows to discriminate between high DNA content and low-DNA content cells. Among high DNA content cells there are double positive vimentin+ keratin+ cells.

Figure 12B:
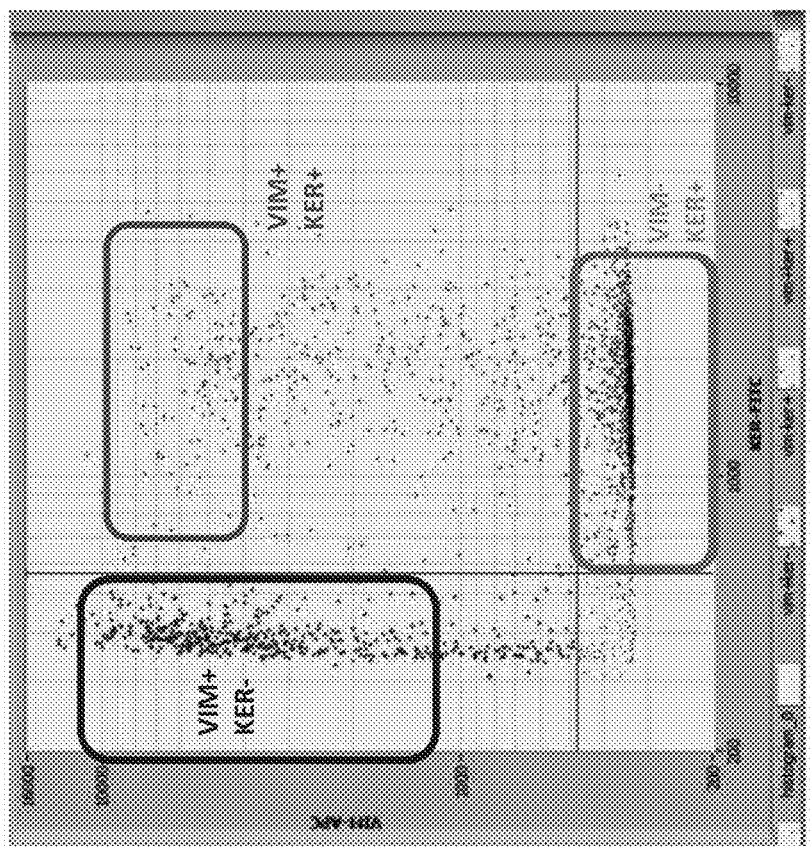
FIG. 12B shows the vimentin/keratin scatter-plot of FIG. 12a, highlighting distinct cell populations.

FIG. 12B shows the scatter-plot of FIG. 12a where 3 populations can clearly be distinguished: vimentin+/keratin−, vimentin−/keratin+ and vimentin+/keratin+. These subpopulations can be further discriminated considering the integral intensity in DAPI, representative of the DNA content, taking as reference the DNA content of the stromal cells main population (located in the vimentin+/keratin− region) (see higher peak of bottom panel in FIG. 11C). Using also integral intensity DAPI comparison with diploid stromal cell population, one can identify vimentin+/keratin− high DNA cells, vimentin+/keratin− low DNA cells (i.e. diploid), vimentin−/keratin+ high DNA cells, vimentin−/keratin+ low DNA cells, vimentin+/keratin+ high DNA cells.

Figure 13:
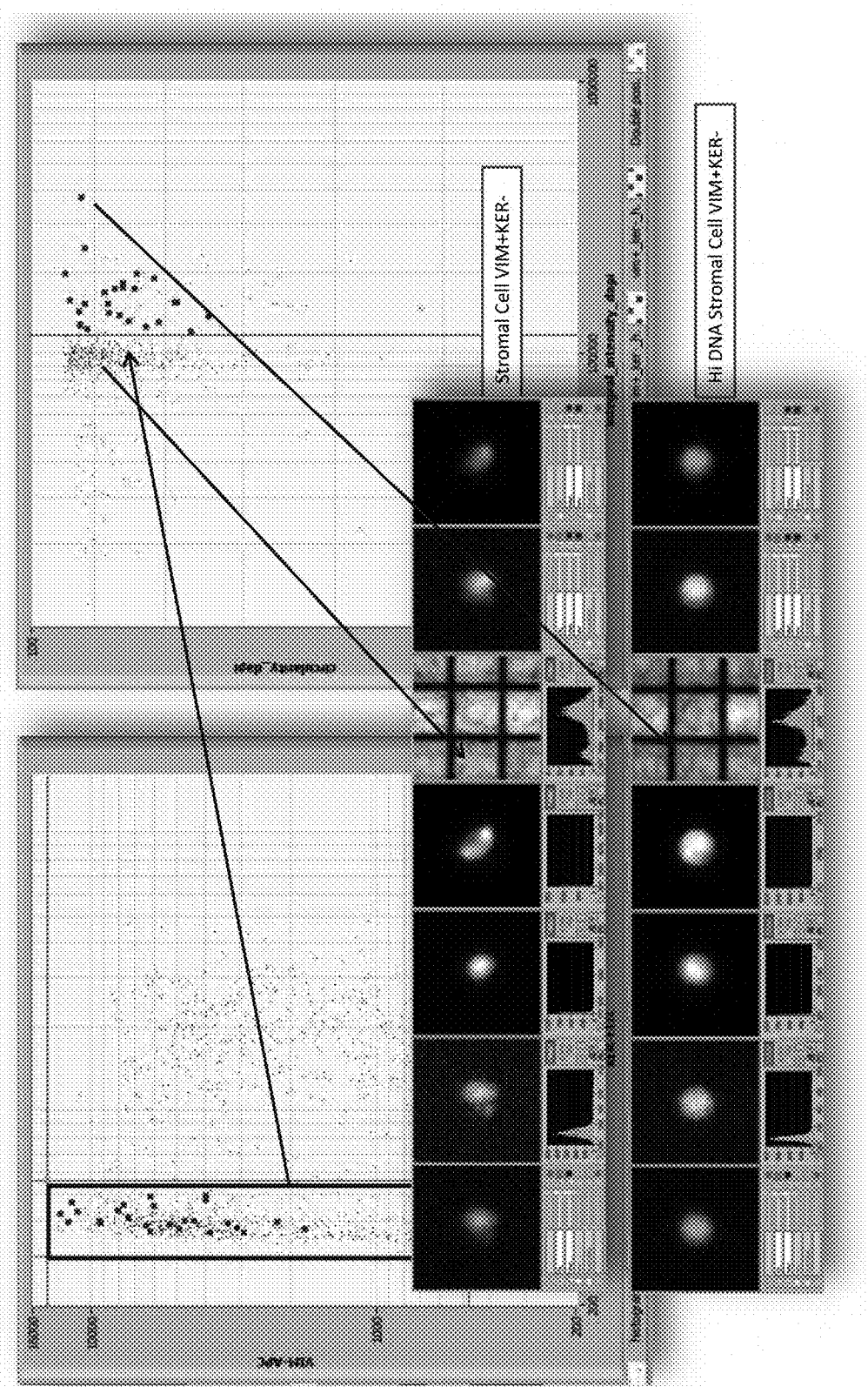
FIG. 13 shows a vimentin/keratin scatter-plot on the left, an integral intensity DAPI scatter on the right and the image-based sorting of two different vimentin+/keratin− events in the panels.

FIG. 13 shows a vimentin/keratin scatter-plot on the left, the integral intensity DAPI scatter on the right and the image-based sorting of two different vimentin+/keratin− events in the panels. The integral intensity DAPI scatter allows to identify cells with a high content of DNA among vimentin+/keratin− events (most of which consist of stromal cells). The image based sorting allows to distinguish true single cells from aggregates of 2 or more normal vimentin+ keratin− cells (by summing the DNA content).

Figure 14:
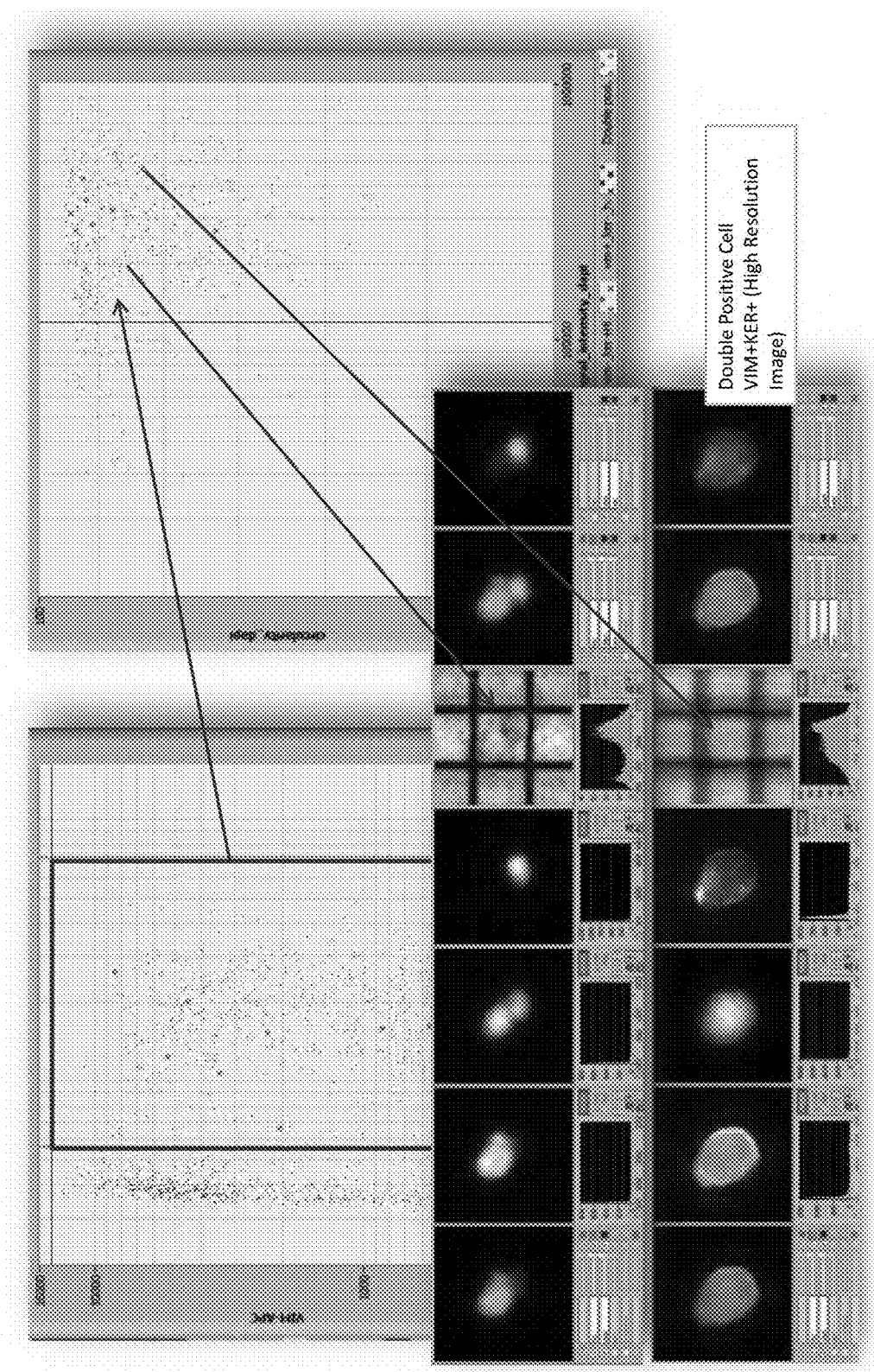
FIG. 14 shows a vimentin/keratin scatter-plot on the left, the integral intensity DAPI scatter on the right, and the image-based sorting of two different vimentin+/keratin+ events in the panels.

FIG. 14 shows a vimentin/keratin scatter-plot on the left, the integral intensity DAPI scatter on the right, and the image-based sorting of two different vimentin+/keratin+ events in the panels. Heterogeneous aggregates (shown in the top inset) including a stromal cell (vimentin+, keratin−) and a tumour cell (vimentin−, keratin+) can be distinguished from double positive cells (vimentin+, keratin+) (bottom inset) by assessing the colocalization of the fluorophores in the image (little or no overlap for heterogenous clusters, coherence and good overlap for single-cells true double-positive cells).

Figure 15:
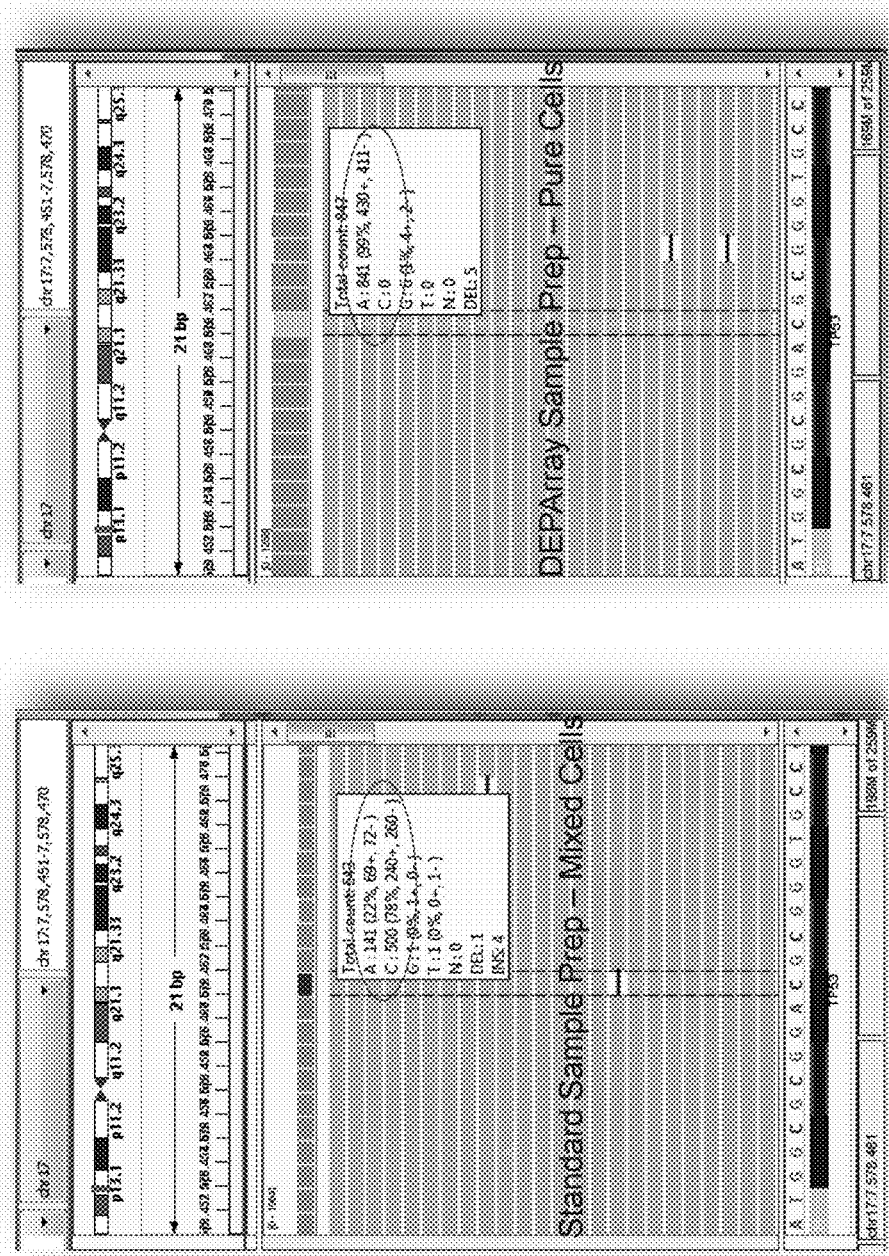
FIG. 15 shows the analysis of mutations by sequencing on standard sample preparations and on DEPArray sample preparations.

Analysis of mutations characteristic of tumours was carried out by targeted next-generation sequencing on standard sample preparations (thus including a mixed population of cells) and on DEPArray sample preparations of pure cells. As can be seen from the results in FIG. 15, the separation between tumour cells and stromal cells allows to obtain a purity of 100%. The frequency of any given mutation (in this case a mutation in the TP53 gene) is identified clearly.

The table in FIG. 16 further shows that a somatic mutations, such as TP53 (COSM10670) can be identified with 100% frequency in tumour cells and 0% frequency in stromal cells when the two population of cells are separated, but unsorted sample only show this mutation as heterozygous. Although in this specific case this somatic muatation was still detected (albeit diluted at 17%-22%), since the percent of tumor cells was sufficiently high, it is clear that in case of lower amounts of tumor cells the signal can be further diluted and become undetectable as it becomes comparable to the background noise of the analytical method.

Interestingly, the separation of tumor and stromal cells allows one to readily detect loss-of-heteozygoisty (LoH), for loci where stromal cells show an heterozygous single-nucleotide polymorphisms (SNPs), with variant frequency around 50%, which become for tumor cells either 0% (e.g. SMAD4 in FIG. 16) or 100% (e.g KDR position 55.980.239 in FIG. 16). This is impossible with the unsorted sample.

Even more interestingly, the separation into homogenous cell populations allows one to detect quantitative traits such as copy-number variations. As an example, EGFR, MET and RET amplification is detectable by the change in variant frequency of the variant allele in heterozygous SNPs located on those genes, which deviates significantly from the 50% found in stromal cells, due to amplification of the variant (EGFR, MET) or wild-type allele (RET), for the sample reported in FIG. 16.

These genetic features cannot instead be identified in unsorted samples including admixed stromal and tumour cells.

In addition, separating the stromal cells allows one to have a profile of germline variants for that sample, which would not be possible for archival samples when only tumor tissue specimens are available (as it usually happens).

Figure 17:
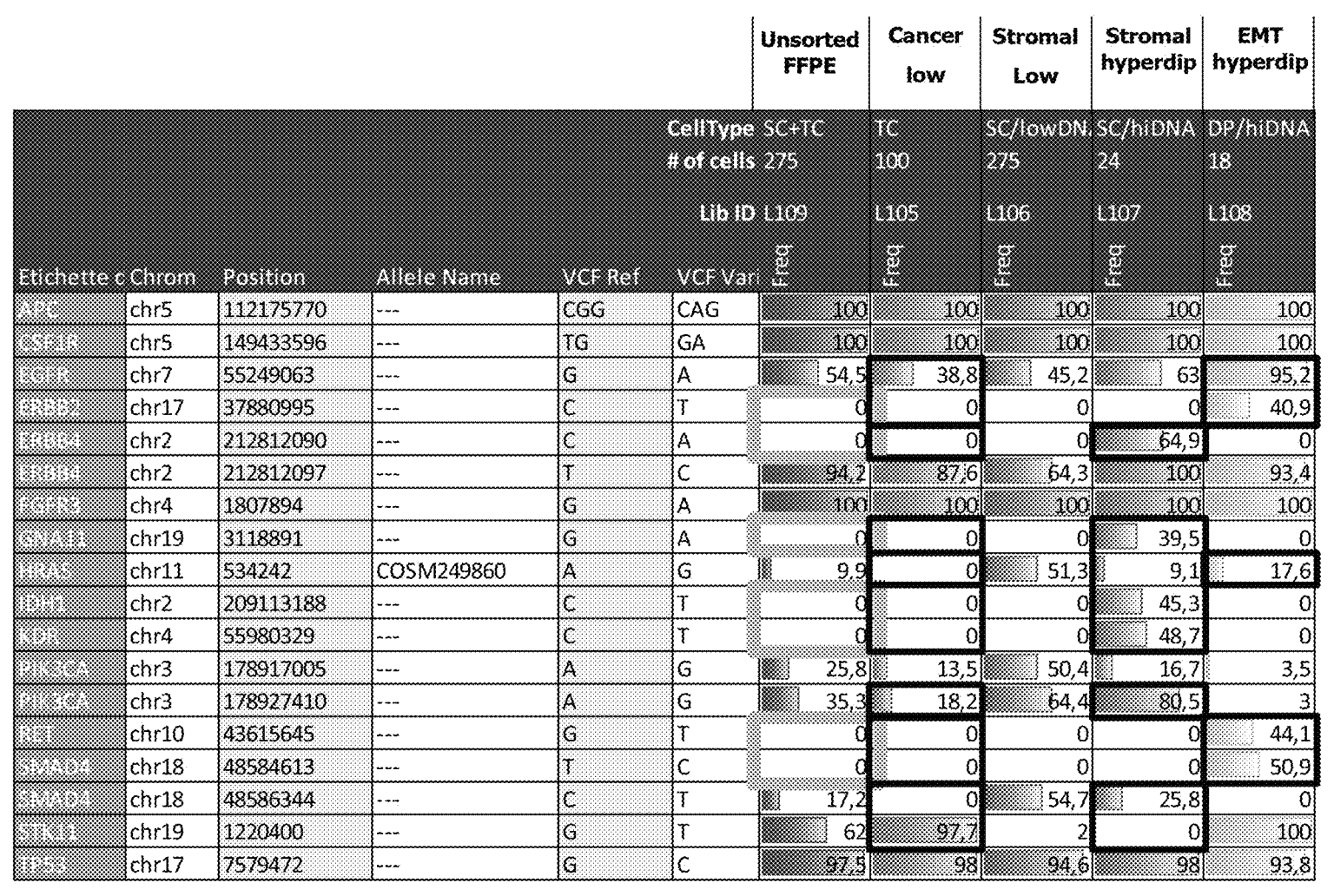

FIG. 17 shows a table summarising data from a lung cancer patient FFPE sorting of cell subtypes. DEPArray™ sorting reveals genetically distinct, rare tumour cells subtypes. As can be noted from the frequency data, variants which are found exclusively in the rare tumour cell subtypes vimentin+/keratin− hyperdiploid cells, indicated as Stromal hyperdiploid (e.g. variants for IDH1, KDR and ERBB4 pos 212812090), and in the double positive vimentin+/keratin+ hyperdiploid, which are cells which have undergone an epithelial to mesenchymal transition—thus indicated as EMT hyperdiploid in figure—(see variants ERBB2, RET, SMAD4 pos 48584613) are undetectable in the unsorted cells. The distribution of these variants shows that those tumor cells are genetically disitinct from the major tumor cell population (vimentin−/keratin+, indicated as Cancer low in the figure).

Additional genetic variant features are also clearly represented at different variant frequency among those pupulations, indicating different copy-number values and LoH patterns.

What is claimed is:

1. A method, comprising the steps of:
a) obtaining a sample of biological fluid comprising cells of interest and other cells, and preparing from the sample a suspension of cells of interest and contaminating cells in a fluid, wherein the cells of interest are nucleated cells and the contaminating cells comprise nucleated cells, the suspension being enriched in cells of interest and the cells of interest being tumour cells;
b) labeling the suspension with:
a first antibody conjugated to a first fluorescent marker that excites at a first wavelength, the first antibody binding to the cells of interest,
a second antibody conjugated to a second fluorescent marker that excites at a second wavelength, the second antibody binding to the contaminating cells and does not bind to the cells of interest, wherein the second antibody is an anti-CD45 antibody or anti-vimentin antibody, and
a third fluorescent marker that binds to the cells of interest, which are nucleated cells, and the nucleated contaminating cells and excites at a third wavelength;
c) introducing the suspension into a single closed chamber of a microfluidic device for containing the entire suspension, wherein the single closed chamber is bounded by a top surface adjacent to at least one electrode and a bottom surface that is flat and adjacent to an array of electrodes;
d) applying to the array of electrodes a first pattern of voltages to generate a first field of force acting on the cells of interest and the contaminating cells to individually trap the cells of interest and the contaminating cells in dielectrophoretic cages;
e) scanning the suspension loaded in the chamber of the microfluidic device with a fluorescent microscope in three different fluorescence channels at first, second, and third wavelengths, respectively, to generate fluorescent images of the cells of interest and the contaminating cells cells of the sample while the cells of interest and the contaminating cells are trapped in the dielectrophoretic cages, the fluorescent images showing morphology of the cells of interest and the contaminating cells and a distribution of three fluorescence signals across the three channels within each of the dielectrophoretic cages;
f) individually selecting single cells of interest in the suspension on the basis of identification in the fluorescent images of a distinct combination of the three signals and morphology compatible with tumor cells, while the single cells of interest are immobilized in the dielectrophoretic cages in the chamber of the microfluidic device, wherein the distinct combination of three signals is positive to the first fluorescent marker, negative to the second fluorescent marker, and positive to the third fluorescent marker; and
g) individually manipulating the selected cells of interest in the single closed chamber of the microfluidic device into a purified specimen by applying to the array of electrodes a second pattern of voltages to generate a second field of force acting only on the selected cells of interest to shift the cells of interest from the dielectrophoretic cages into the purified specimen or applying an optical force acting only on the selected cells of interest to shift the cells from the dielectrophoretic cages to the purified specimen,
wherein:
the purified specimen has a purity of at least 90% as defined by the ratio of the number of the cells of interest to the total number of cells in the purified specimen.

2. The method of claim 1, wherein the purified specimen has a purity of at least 95%.

3. The method of claim 2, wherein the purified specimen has a purity of 100%.

4. The method of claim 1, wherein said microfluidic system isolates said cells of interest in a non-manual way.

5. The method of claim 4, wherein said microfluidic system isolates said cells of interest in an automatic or semi-automatic way.

6. The method of claim 1, wherein said individual selection of single cells of interest is made on the basis of parameters evaluated in the absence of flow of fluid.

7. The method of claim 1, wherein the sample is a sample of organic fluid, the method comprising a step of enriching said sample of organic fluid in at least one population of cells comprising said at least one tumour cell, before the step of obtaining a purified sample.

8. The method of claim 7, wherein said step of enriching said sample of organic fluid comprises a selection of cells made on the basis of at least one parameter chosen in the group consisting of:

a. mass density;
b. morphology;
c. electrical properties;
d. chemical properties;
e. mechanical properties;
f. expression of surface antigens;
g. expression of intracytosolic antigens;
h. dielectric properties;
i. magnetic properties;
j. optical properties;
k. geometrical properties; and
l. combinations thereof.

9. The method of claim 7, wherein said step of enriching said sample of organic fluid comprises the step of treating said sample of organic fluid to separate and recover the nucleated cells and enrich said sample subsequently in nucleated cells.

10. The method of claim 9, wherein said step of enriching said sample of organic fluid comprises at least the step of centrifuging said sample of organic fluid in a density gradient.

11. The method of claim 9, wherein said step of enriching said sample of organic fluid comprises the step of carrying out a selective lysis of the erythrocytes.

12. The method of claim 7, wherein said step of enriching said sample of organic fluid comprises the step of carrying out a positive and/or negative selection via magnetic beads coupled to antibodies according to at least one of the following modalities:
 a) CD45 negative;
 b) CD45 and GPA negative;
 c) CD45 and CD14 negative;
 d) CD45, CD14 and GPA negative;
 e) EpCAM positive; and
 f) CK positive.

13. The method of claim 7, wherein said step of enriching is performed in combination with said step of obtaining a purified specimen within the same microfluidic device used for performing the step of obtaining a purified specimen.

14. The method of claim 13, wherein said microfluidic device is used equipped with a plurality of different chambers, separated from one another and hydraulically connected, delimited on at least one face by a single chip or by a plurality of separate chips.

15. The method of claim 1, comprising a step of further labelling the cells of interest with at least one type of tracer.

16. The method of claim 15, wherein said at least one type of tracer is a fluorescence in situ hybridization (FISH) probe.

17. The method of claim 15, wherein said at least one type of tracer is an antibody conjugated with a marker selected from the group consisting of:
 fluorophors;
 chromogens;
 fluorescent microbeads; and
 non-fluorescent microbeads.

18. The method of claim 1, wherein said first antibody recognizes an antigen selected from the group consisting of:
 EpCAM;
 Cytokeratin;
 prostate specific antigen (PSA);
 TF1; and
 HER2/neu.

19. The method of claim 1, wherein said sample is a formalin fixed and paraffin embedded (FFPE) biopsy sample.

20. The method of claim 19, wherein preparing the suspension sample comprises first subjecting the FFPE biopsy sample to deparaffinization and then dissociating single cells of the FFPE biopsy sample with a 1% dispase/ 1% collagenase 1a solution.

21. The method of claim 1, wherein individually manipulating the selected cells of interest comprises applying to the array of electrodes the second pattern of voltages to apply the second field of force acting only on the selected cells of interest to shift the cells of interest from the dielectrophoretic cages into the purified specimen.

22. A method, comprising the steps of:
 a) obtaining a sample of a biological fluid and preparing from the sample a suspension of cells of interest and contaminating cells in a fluid wherein the cells of interest are nucleated cells and the contaminating cells comprise nucleated cells, the cells of interest being circulating tumour cells and/or disseminating tumour cells;
 b) labeling the suspension with:
  a first antibody conjugated to a first fluorescent marker that excites at a first wavelength, the first antibody binding to the cells of interest, wherein the first antibody is an anti-cytokeratin antibody, an anti-EpCAM antibody, an anti-PSA antibody, an anti-TTF-1 antibody, or an anti-HER2/neu antibody,
  a second antibody conjugated to a second fluorescent marker that excites at a second wavelength, the second antibody binding to the contaminating cells and does not bind to the cells of interest, wherein the second antibody is an anti-CD45 antibody, and,
  a third fluorescent marker that binds to the cells of interest, which are nucleated cells, and to the nucleated contaminating cells and excites at a third wavelength;
 c) introducing the suspension into a chamber of a microfluidic device, wherein the chamber is bounded by a top surface adjacent to at least one electrode and a bottom surface that is adjacent to an array of electrodes arranged in the chamber to generate dielectrophoretic cages and immobilize the cells of interest and the contaminating cells in the chamber using dielectrophoretic cages;
 d) applying a first pattern of voltages to the array of electrodes to generate a first field of force acting on the cells of interest and the contaminating cells to individually trap the cells of interest and contaminating cells in the dielectrophoretic cages;
 e) scanning the suspension loaded in the chamber of the microfluidic device with a fluorescence microscope in three different fluorescence channels at first, second, and third wavelengths, respectively, to generate fluorescent images of the cells of interest and the contaminating cells of the suspension while the cells of interest and the contaminating cells are trapped in the dielectrophoretic cages, the fluorescent images showing morphology of the cells of interest and the contaminating cells, and a distribution of three fluorescence signals across the three channels within each of the dielectrophoretic cages;
 f) individually selecting single cells of interest in the suspension on the basis of identification in the fluorescent images of a distinct combination of the three signals and morphology compatible with tumour cells, while the single cells of interest are immobilized in the dielectrophoretic cages in the chamber of the microfluidic device, wherein the distinct combination of the three signals is positive to the first fluorescent marker, negative to the second fluorescent marker, and positive to the third fluorescent maker; and g) individually manipulating the selected cells of interest immobilized in the chamber of the microfluidic device into a purified specimen using dielectrophoretic isolation by applying a second pattern of voltages to the array of electrodes to generate a second field of force acting only on the selected cells of interest to shift the selected cells of interest from the dielectrophoretic cages into the purified specimen, wherein:
the purified specimen has a purity of at least 90% as defined by the ratio of the number of the cells of interest to the total number of cells in the purified specimen.

23. The method of claim 22, wherein the first antibody is an anti-cytokeratin antibody or an anti-EpCAM antibody.

24. The method of claim 22, wherein the cells of interest are prostate cancer cells and the first antibody is an anti-PSA antibody.

25. The method of claim 22, wherein the cells of interest are lung cancer cells and the first antibody is an anti-TTF-1 antibody.

26. The method of claim 22, wherein the cells of interest are breast cancer cells and the first antibody is an anti-HER2 antibody.

27. A method, comprising the steps of:
a) labeling a suspension comprising cells of interest and contaminating cells, the suspension being enriched in cells of interest and the cells of interest being circulating tumor cells and/or disseminating tumour cells, wherein the cells of interest are nucleated cells and the contaminating cells comprise nucleated cells, with:
a first antibody conjugated to a first fluorescent marker that excites at a first wavelength, the first antibody binding to the cells of interest,
a second antibody conjugated to a second fluorescent marker that excites at a second wavelength, the second antibody binding to the contaminating cells and does not bind to the cells of interest, wherein the second antibody is an anti-CD45 antibody or anti-vimentin antibody, and,
a third fluorescent marker that binds to the cells of interest, which are nucleated cells, and nucleated contaminating cells and excites at a third wavelength; ;
b) introducing the suspension into a chamber of a microfluidic device, wherein the chamber is bounded by a top surface adjacent to at least one electrode and a bottom surface that is adjacent to an array of electrodes arranged in the chamber to generate dielectrophoretic cages and immobilize the cells of interest and the contaminating cells in the chamber using dielectrophoretic cages;

c) applying a first pattern of voltages to the array of electrodes to generate a first field of force acting on the cells of interest and the contaminating cells, to individually trap the cells of interest and the contaminating cells in the dielectrophoretic cages;

d) scanning the suspension loaded in the chamber of the microfluidic device with a fluorescence microscope in three different fluorescence channels at first, second, and third wavelengths, respectively, to generate fluorescent images of the cells of interest and the contaminating cells while the cells of interest and the contaminating cells, are trapped in the dielectrophoretic cages, the fluorescent images showing morphology of the cells of interest and the contaminating cells, and a distribution of three fluorescence signals across the three channels within each of the dielectrophoretic cages;

e) individually selecting single cells of interest in the suspension on the basis of identification in the fluorescent images of a distinct combination of the three signals and morphology compatible with tumour cells, while the single cells of interest are immobilized in the dielectrophoretic cages in the chamber of the microfluidic device, wherein the distinct combination of the three signals is positive to the first fluorescent marker, negative to the second fluorescent marker, and positive to the third fluorescent maker; and f) individually manipulating the selected cells of interest immobilized in the chamber of the microfluidic device into a purified specimen using dielectrophoretic isolation by applying a second pattern of voltages to the array of electrodes to generate a second field of force acting only on the selected cells of interest to shift the selected cells of interest from the dielectrophoretic cages into the purified specimen, wherein:
the purified specimen has a purity of at least 90% as defined by the ratio of the number of the cells of interest to the total number of cells in the purified specimen.

28. The method of claim 27, wherein the first antibody is an anti-cytokeratin antibody, an anti-EpCAM antibody, an anti-PSA antibody, an anti-TTF-1 antibody, or an anti-HER2/neu antibody.

* * * * *